United States Patent
Filip

(10) Patent No.: US 11,384,057 B2
(45) Date of Patent: Jul. 12, 2022

(54) METHODS FOR PREPARING FUEL ADDITIVES

(71) Applicant: BP OIL INTERNATIONAL LIMITED, Middlesex (GB)

(72) Inventor: Sorin Vasile Filip, Reading (GB)

(73) Assignee: BP OIL INTERNATIONAL LIMITED, London (GB)

( * ) Notice: Subject to any disclaimer, the term of this patent is extended or adjusted under 35 U.S.C. 154(b) by 6 days.

(21) Appl. No.: 16/958,733

(22) PCT Filed: Dec. 19, 2018

(86) PCT No.: PCT/EP2018/086025
§ 371 (c)(1),
(2) Date: Jun. 28, 2020

(87) PCT Pub. No.: WO2019/129591
PCT Pub. Date: Jul. 4, 2019

(65) Prior Publication Data
US 2020/0331869 A1    Oct. 22, 2020

(30) Foreign Application Priority Data
Dec. 27, 2017  (GB) .................... 1721964

(51) Int. Cl.
*C07D 267/14*  (2006.01)
*C10L 1/233*  (2006.01)
*C10L 10/10*  (2006.01)

(52) U.S. Cl.
CPC ............ *C07D 267/14* (2013.01); *C10L 1/233* (2013.01); *C10L 10/10* (2013.01); *C10L 2270/023* (2013.01)

(58) Field of Classification Search
CPC .... C10L 1/233; C10L 10/10; C10L 2270/023; C07D 267/14
See application file for complete search history.

(56) References Cited

U.S. PATENT DOCUMENTS

| | | | |
|---|---|---|---|
| 4,288,589 | A | 9/1981 | Loew et al. |
| 4,861,914 | A | 8/1989 | Weidig et al. |
| 8,222,417 | B2 | 7/2012 | Suzuki et al. |
| 2005/0261244 | A1 | 11/2005 | Tuerdi et al. |
| 2006/0123696 | A1 | 6/2006 | Gaughan et al. |
| 2008/0064871 | A1 | 3/2008 | Hirata et al. |
| 2009/0094887 | A1 | 4/2009 | Calvert et al. |

FOREIGN PATENT DOCUMENTS

| | | | |
|---|---|---|---|
| CN | 105272904 | A | 4/2019 |
| EP | 2172453 | A1 | 4/2010 |
| EP | 3205701 | A1 | 8/2017 |
| EP | 3205703 | A1 | 8/2017 |
| GB | 1013572 | * | 12/1965 |
| GB | 1013572 | A | 12/1965 |
| GB | 2026524 | A | 2/1980 |
| JP | H04247017 | A | 9/1992 |
| KR | 20120102381 | A | 9/2012 |
| WO | 2009001817 | A1 | 12/2008 |
| WO | 2011048112 | A1 | 4/2011 |
| WO | 2011103460 | A1 | 8/2011 |
| WO | 2012009678 | A1 | 1/2012 |
| WO | 2014047390 | A1 | 3/2014 |
| WO | 2015063694 | A1 | 5/2015 |
| WO | 2017108723 | A2 | 6/2017 |
| WO | 2017137518 | A1 | 8/2017 |
| WO | 2017142833 | A1 | 8/2017 |

OTHER PUBLICATIONS

Shadyro, O.I. et al. "Synthesis and Antiviral Activity of N-Acyl Derivatives of 4,6-Di-(tert-butyl)-2-aminophenol." Pharmaceutical Chemistry Journal. 2002, 36(8), p. 410-412.
Perry, B. et al. "Achieving multi-isofrom-PI3K inhibition in a series of substituted 3,4-dihydro-2H-benzo[1,4] oxazines." Bioorg Med Chem Lett. 2008, 18, 16, p. 4700-4704.
Dugar, S. et al. "A Concise and Efficient Synthesis of Substituted Morpholines." Synthesis. 2014, 47, 5, p. 712-720.
International Search Report and Written Opinion of International Application No. PCT/EP2018/086022, dated Apr. 10, 2019.
Coudert, G. et al. "A new synthesis of 3,4-dihydro-2H-1,4-benzoxazines using solid-liquid phase-transfer catalysis." Synthesis Georg Thieme Verlag. 1979, 7, p. 541-543.

(Continued)

*Primary Examiner* — Cephia D Toomer
(74) *Attorney, Agent, or Firm* — McDonnell Boehnen Hulbert & Berghoff LLP

(57) ABSTRACT

A method is provided for preparing a fuel additive having the formula: (1) The method comprises carrying out the following reactions: (i) addition of an alkylating agent b to starting material a: (a) to form an intermediate c; and (ii) ring closing intermediate c to form fuel additive e.

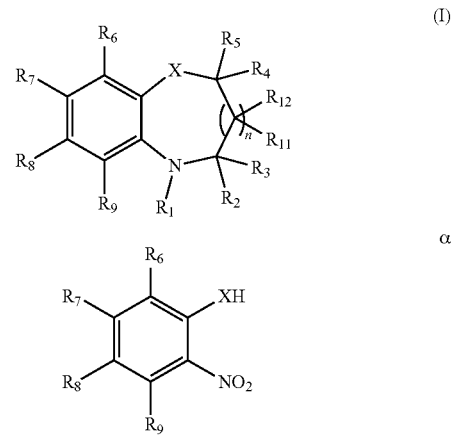

18 Claims, No Drawings

(56) References Cited

OTHER PUBLICATIONS

Kotha, S. "Synthesis and Reactions of 3,4-dihydro-2H-1,4-benzoxazine Derivatives." Heterocycles. 1994, 38, p. 5-8.
Hernandez-Olmos, V. et al. "N-Substituted Phenoxazine and Acridone Derivatives: Structure-Activity Relationships of Potent P2X4 Receptor Antagonists." J. Med. Chem. 2012, 55, 22, p. 9576-9588.
Bunce, R.A. et al. "Tetrahydro-1,5-benzoxazepines and tetrahydro-1H-1,5-benzodiazepines by a tandem reduction-reductive amination reaction." J. Heterocyclic Chem. 2004, 41, 6, p. 963-970.
Shadyro, O.I. et al. "Synthesis and Antiviral Activity of N-Acyl Derivatives of 4,6-Di-(tert-butyl)-2-aminophenol." Pharmaceutical Chemistry Journal. 2003, 37, p. 399-401.
International Search Report and Written Opinion for International Application No. PCT/EP2018/086023, dated Jul. 4, 2019.
International Search Report and Written Opinion for International Application No. PCT/EP2018/086027, dated May 10, 2019.
Filippou, P.S. et al. "Regulation of the *Escherichia coli* AtoSC two component system by synthetic biologically active 5;7;8-trimethyl-1;4-benzoxazine analogues." Bioorgan Med Chem. 2011, 19, 16, p. 5061-5070.
Ramesh, C. et al. "A simple and facile route for the synthesis of 2H-1,4-benzoxazin-3-(4H)-ones via reductive cyclization of 2-(2-nitrophenoxy)acetonitrile adducts in the presence of Fe/acetic acid." Tetrahedron. 2011, 67, 6, p. 1187-1192.
Reddy, Ch. R. et al. "Reductive N-alkylation of aromatic amines and nitro compounds with nitriles using polymethylhydrosiloxane." Tetrahedron Let. 2007, 48, 15, p. 2765-2768.
International Search Report and Written Opinion for International Application No. PCT/EP2018/086025, dated Jun. 6, 2019.
Bartsch, H. et al. "Synthese und Reaktivität von 2—und 3-hydroxylierten Dihydro-1,4-Benzoxazinen." Monatshefte für Chemie. 1997, 110, p. 267-278.
Mizar, P. et al. "Synthesis of substituted 4-(3-alkyl-1,2,4-oxadiazol-5-ylmethyl)-3,4-dihydro-2H-1,4-benzoxazines and 4-(1H-benzimidazol-2-ylmethyl)-3,4-dihydro-2H-1,4-benzoxazines." Tetrahedron Let. 2006, 47, 44, p. 7823-7826.
Fu, Y. et al. "Simple and efficient synthesis of novel N-dichloroacetyl-3,4-dihydro-2H-1,4-benzoxazines." Heterocycl Commun. 2012, 18, 3, p. 143-146.
International Search Report and Written Opinion for International Application No. PCT/EP2018/086024, dated Jun. 6, 2019.
Knorr, L. "Synthesen in der »Oxazinreihe«." Ber. Dtsch. Chem. Ges. 1889, 22, p. 2081-2099.
Calderone, V. et al "Structural modifications of benzanilide derivatives, effictive potassium channel openers. X." Eur. J. Med. Chem. 2006, 41(12), p. 1421-1429.
Liu, Y. et al. "Concise synthesis of 3,4-dihydro-1,4-benzoxazines by three-component reactions of acyl chlorides, o-aminophenols and 1,2-dichloroethane." Tetrahedron. 2018, 74(27), p. 3691-3696.
Huerta, G. et al. "Facile Synthesis of Aminoalcohols by Ring Opening of Epoxides Under Solvent Free Conditions." Synthetic Commun. 2004, 34(13), p. 2393-2406.
Woydowski, K. "Optically Active Heterocycles through Ring Transformations on Oxirane3-carboxylate Derivatives." Sel. Org. React. Database (SORD). 1999. See CASREACT abstract accession No. 161 :698073.
Gao, S. et al. "Synthesis and crystal structure of N-dichloroacetyl-3,4-dihydro-3-methyl-6-chloro-2H-1,4-benzoxazine". Journal of Chemistry. 2015, 2015, Article ID 268306, p. 1-5.
Yang, J. et al. "Synthesis, anti-cancer evaluation of benzenesulfoamide derivates as potent tubulin-targeting agents." Eur. J. Med. Chem. 2016, 122, p. 488-496.

\* cited by examiner

METHODS FOR PREPARING FUEL ADDITIVES

This application is a national stage application under 35 U.S.C. § 371 of International Application No. PCT/EP2018/086025, filed Dec. 19, 2018, which claims priority to Great Britain Application No. 1721964.3, filed Dec. 27, 2017, the disclosures of which are explicitly incorporated by reference herein.

FIELD OF THE INVENTION

This invention relates to methods for preparing octane-boosting additives for use in a fuel for a spark-ignition internal combustion engine. In particular, the invention relates to methods for preparing octane-boosting additives that are derivatives of benzo[1,4]oxazines and 1,5-benzoxazepines. The invention further relates to methods for preparing fuels for a spark-ignition internal combustion engine comprising the octane-boosting additives.

BACKGROUND OF THE INVENTION

Spark-ignition internal combustion engines are widely used for power, both domestically and in industry. For instance, spark-ignition internal combustion engines are commonly used to power vehicles, such as passenger cars, in the automotive industry.

Fuels for a spark-ignition internal combustion engine (generally gasoline fuels) typically contain a number of additives to improve the properties of the fuel.

One class of fuel additives is octane-improving additives. These additives increase the octane number of the fuel which is desirable for combatting problems associated with pre-ignition, such as knocking. Additisation of a fuel with an octane improver may be carried out by refineries or other suppliers, e.g. fuel terminals or bulk fuel blenders, so that the fuel meets applicable fuel specifications when the base fuel octane number is otherwise too low.

Organometallic compounds, comprising e.g. iron, lead or manganese, are well-known octane improvers, with tetraethyl lead (TEL) having been extensively used as a highly effective octane improver. However, TEL and other organometallic compounds are generally now only used in fuels in small amounts, if at all, as they can be toxic, damaging to the engine and damaging to the environment.

Octane improvers which are not based on metals include oxygenates (e.g. ethers and alcohols) and aromatic amines. However, these additives also suffer from various drawbacks. For instance, N-methyl aniline (NMA), an aromatic amine, must be used at a relatively high treat rate (1.5 to 2% weight additive/weight base fuel) to have a significant effect on the octane number of the fuel. NMA can also be toxic. Oxygenates give a reduction in energy density in the fuel and, as with NMA, have to be added at high treat rates, potentially causing compatibility problems with fuel storage, fuel lines, seals and other engine components.

Recently, a new class of octane-boosting additive has been discovered. These octane-boosting additives are derivatives of benzo[1,4]oxazines and 1,5-benzoxazepine, and show great promise due to their non-metallic nature, their low oxygenate content, and their efficacy at low treat rates (see WO 2017/137518).

Synthesis routes currently reported in the literature provide various descriptions of how benzoxazines could be prepared on a relatively small scale (hundreds of mg to up to 100 kg scale). For example, US 2008/064871—which relates to compounds for the treatment or prophylaxis of diseases relating to uric acid, such as gout—discloses the preparation of benzoxazine-derived compounds.

However, such synthesis methods are not viable for preparing the new class of octane-boosting additives on an industrial scale, e.g. from 50 to up to 20,000 tonnes per year, due to the high cost of specialised raw materials, e.g. methylaminophenols, and reagents, e.g. lithium aluminium hydride and dibromoethane, which are required in stoichiometric amounts.

Accordingly, there is a need for methods for synthesising the new class of octane-boosting additives that may be implemented on a large scale and which mitigate at least some of the problems highlighted above, e.g. by avoiding the use of costly aminophenol starting materials.

SUMMARY OF THE INVENTION

It has now been found that the new class of octane-boosting additives can be prepared from starting materials derived from nitrophenols and nitroanilines. Accordingly, the present invention provides a method for preparing a fuel additive e having the formula:

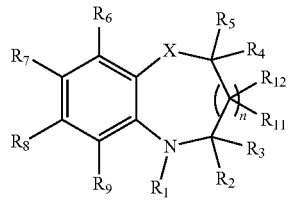

where: $R_1$ is hydrogen;

$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;

$R_6$, $R_7$, $R_8$ and $R_9$ are each independently selected from hydrogen, alkyl, alkoxy, alkoxy-alkyl, secondary amine and tertiary amine groups;

X is selected from —O— or —$NR_{10}$—, where $R_{10}$ is selected from hydrogen and alkyl groups; and n is 0 or 1.

The method comprises carrying out the following reaction:

(i) addition of an alkylating agent b to starting material a:

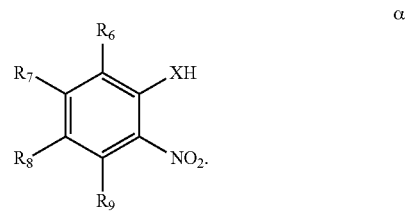

to form an intermediate c; and (ii) ring closing intermediate c to form fuel additive e, wherein the alkylating agent b and intermediate c are selected from:

| alkylating agent b | intermediate c |
|---|---|
| (1) [structure with $R_5$, $R_4$, $R_{12}$, $R_{11}$, L, CN] | [structure with $R_6$, $R_7$, $R_8$, $R_9$, X, $NO_2$, $R_5$, $R_4$, $R_{12}$, $R_{11}$, CN] |
| (2) [bis-L structure with $R_5$, $R_4$, $R_{12}$, $R_{11}$, $R_3$, $R_2$] | [structure with $R_6$, $R_7$, $R_8$, $R_9$, X, $NO_2$, $R_5$, $R_4$, $R_{12}$, $R_{11}$, $R_2$, $R_3$, L] |
| (3) [structure with $R_5$, $R_4$, $R_{12}$, $R_{11}$, $R_2$, L, $R_{13}O$, $R_{13}O$] | [structure with $R_6$, $R_7$, $R_8$, $R_9$, X, $NO_2$, $R_5$, $R_4$, $R_{12}$, $R_{11}$, $R_2$, $OR_{13}$, $OR_{13}$] |
| (4) [oxetane with $R_5$, $R_4$, $R_{12}$, $R_{11}$, $R_3$, $R_2$] | [structure with $R_6$, $R_7$, $R_8$, $R_9$, X, $NO_2$, $R_5$, $R_4$, $R_{12}$, $R_{11}$, $R_2$, $R_3$, OH] |
| (5) [structure with $R_5$, $R_4$, $R_{12}$, $R_{11}$, L, $R_{14}O$, C(=O)] | [structure with $R_6$, $R_7$, $R_8$, $R_9$, X, $NO_2$, $R_5$, $R_4$, $R_{12}$, $R_{11}$, $OR_{14}$, C(=O)] |
| (6) [structure with $R_5$, $R_4$, $R_{12}$, $R_{11}$, L, CHO] | [structure with $R_6$, $R_7$, $R_8$, $R_9$, X, $NO_2$, $R_5$, $R_4$, $R_{12}$, $R_{11}$, CHO] | where: each L in alkylating agent b is independently selected from leaving groups or both L groups together form the group —O—C(O)—O—;
each $R_{13}$ is independently selected from hydrogen and alkyl groups, or both $R_{13}$ groups together with the —O—C—O— group to which they are attached form a 1,3-dioxolane or 1,3-dioxane group; and
$R_{14}$ is selected from hydrogen and alkyl groups.

Also provided is a fuel additive e which is obtainable by a method of the present invention.

The present invention further provides a process for preparing a fuel for a spark-ignition internal combustion engine. The process comprises:
preparing a fuel additive using a method of the present invention; and
blending the fuel additive with a base fuel.

A fuel for a spark-ignition internal combustion engine is also provided. The fuel comprises a fuel additive e of the present invention and a base fuel.

DETAILED DESCRIPTION OF THE INVENTION

The present invention provides a method for preparing a fuel additive.

In step (i) of the method, an alkylating agent b is added to starting material a to form an intermediate c:

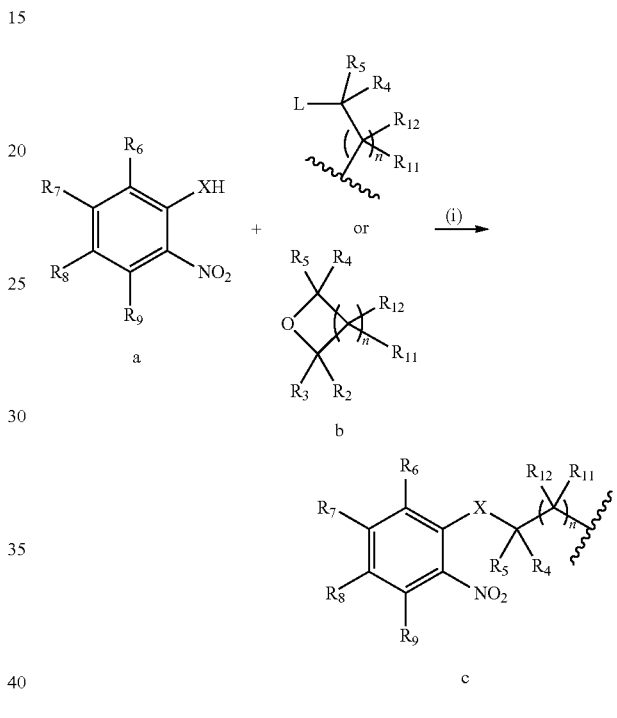

In embodiment (1), the alkylating agent b is:

[structure with L, $R_5$, $R_4$, $R_{12}$, $R_{11}$, CN]

and the intermediate c is:

[structure with $R_6$, $R_7$, $R_8$, $R_9$, X, $NO_2$, $R_5$, $R_4$, $R_{12}$, $R_{11}$, CN]

This embodiment is particularly preferred.

In embodiment (2), the alkylating agent b is:

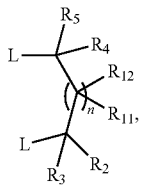

and the intermediate c is:

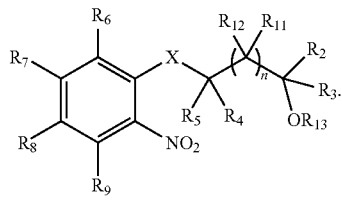

Preferably, the alkylating agent b is an epoxide reagent, i.e. n=0, since epoxides readily react with starting material a to form intermediate c.

In embodiment (5), the alkylating agent b is:

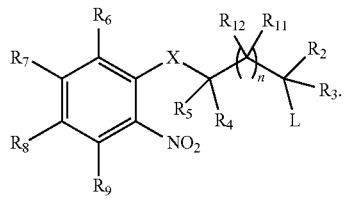

and the intermediate c is:

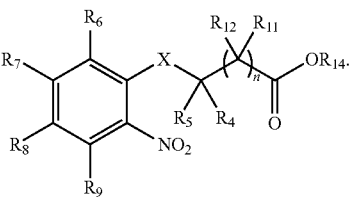

In embodiment (3), the alkylating agent b is:

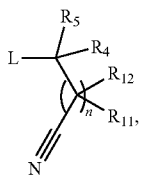

and the intermediate c is:

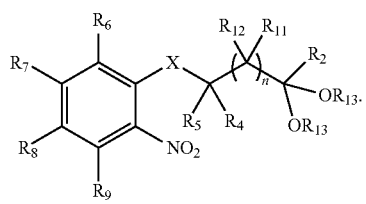

$R_{14}$ is selected from hydrogen and alkyl groups, and preferably from hydrogen, methyl, ethyl, propyl and butyl groups, and more preferably from hydrogen, methyl and ethyl groups.

In embodiment (6), the alkylating agent b is:

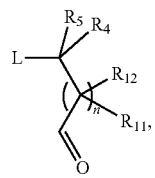

and the intermediate c is:

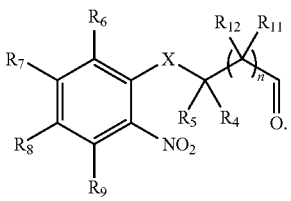

Each $R_{13}$ is independently selected from hydrogen and alkyl groups, or both $R_{13}$ groups together with the —O—C—O— group to which they are attached form a 1,3-dioxolane or 1,3-dioxane group. Each $R_{13}$ is preferably selected from hydrogen, methyl, ethyl, propyl and butyl groups, and more preferably from methyl and ethyl groups. In preferred embodiments, the $R_{13}$ groups are the same.

In embodiment (4), the alkylating agent b is:

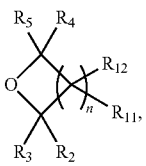

During step (i), a leaving group L is lost from alkylating agent b. Each L in alkylating agent b is independently selected from leaving groups or both L groups together form the group —O—C(O)—O—, a group which effectively provides two leaving groups. It will be appreciated that it is only in embodiment (2) that two L groups are present and, thus, together can form the group —O—C(O)—O—.

Preferably, each L is independently selected from: halides (e.g. Cl, Br, I), sulfonates (e.g. —OSO$_2$A, where A is selected from tolyl, methyl, —CF$_3$, —CH$_2$Cl, phenyl and p-nitrophenyl), substituted aryloxy groups (e.g. —O—Ar, where Ar is selected from nitro-substituted aryl groups such as p-nitrophenyl) and hydroxy groups, more preferably from halides and sulfonates, and most preferably from Cl and Br. Hydroxy groups will generally only be used as a possible leaving group L in embodiment (2).

Generally, the alkylating agent b may be used in an amount of from 0.5 to 8 molar equivalents, preferably from 0.75 to 6 molar equivalents, and more preferably from 0.85 to 5 molar equivalents, as compared to starting material a. It will be appreciated that the preferred proportions of starting material a and alkylating agent b may vary between the different embodiments. For instance, with embodiment (1), alkylating agent b may preferably used in an amount of from 0.85 to 0.95 molar equivalents. With embodiment (2), alkylating agent b may preferably be used in an amount of from 2 to 5 molar equivalents.

Step (i) of the present invention is preferably carried out in the presence of a base. This is particularly the case with embodiments (1), (2) particularly in instances other than where both L groups together form the group —O—C(O)—O— or both of the L groups are selected from —OH, (3), (5) and (6). Suitable bases may be selected from:

inorganic bases, e.g. alkali metal hydroxides (such as sodium hydroxide and potassium hydroxides) and carbonates (such as sodium bicarbonate, sodium carbonate, potassium bicarbonate and potassium carbonate), ammonia, and organic bases, e.g. nitrogen-containing organic bases, such as from trimethylamine, diisopropylethylamine, 1,8-diazabicyclo[5.4.0]undec-7-ene, pyridine and 4-dimethylaminopyridine.

The base is preferably an inorganic base and more preferably selected from carbonates.

The base is preferably used in an amount of from 0.8 to 5 molar equivalents, preferably from 1 to 3 molar equivalents, and more preferably from 1.05 to 2.5 molar equivalents as compared to starting material a.

In some embodiments, step (i) may be carried out in the presence of a catalyst, e.g. a catalyst selected from acids (e.g. p-toluene sulfonic acid or sodium hydrogen sulphite), zeolites (e.g. zeolite Y, sodium (faujasite)), metal catalysts (e.g. a palladium catalyst, preferably used with a zinc oxide support), halogen exchange catalysts (e.g. alkali metal halides, such as KBr, NaBr, KI and NaI) and phase transfer catalysts (e.g. a quaternary ammonium salt such as tetraalkylammonium halides, preferably butyltriethylammonium chloride or methyltributylammonium chloride).

For instance, in embodiment (2) where both L groups together form the group —O—C(O)—O—, or where at least one of the L groups is selected from —OH, then a catalyst is preferably used and is preferably selected from an acid (e.g. p-toluene sulfonic acid or sodium hydrogen sulphite), a zeolite (e.g. zeolite Y, sodium (faujasite)) or a metal catalyst (e.g. a palladium catalyst, preferably used with a zinc oxide support).

Step (i) may also be carried out in the presence of a catalyst in embodiments in which L is a halogen, particularly where L is Cl, for instance in the presence of at least one of, and preferably both of, a halogen exchange catalyst (e.g. alkali metal halides, such as KBr, NaBr, KI and NaI) and a phase transfer catalyst (e.g. a quaternary ammonium salt such as tetraalkylammonium halides, preferably butyltriethylammonium chloride or methyltributylammonium chloride).

The catalyst may be used in an amount of less than 1 molar equivalent, preferably less than 0.5 molar equivalents, and more preferably less than 0.1 molar equivalents as compared to starting material a.

It will be appreciated that both a base and a catalyst may be used. An example of such a combination is an inorganic base (e.g. an alkali metal carbonate) and a halogen exchange catalyst (e.g. an alkali metal iodide).

Step (i) may be carried out in the presence of a solvent selected from aprotic solvents (e.g. tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile), chlorinated solvents (e.g. dichloromethane, dichloroethane, chloroform) and water. Aprotic solvents are well-known in the art as solvents which are not capable of donating protons. Aprotic solvents do not contain hydrogen atoms bound to a nitrogen or an oxygen.

Preferably, step (i) is carried out in the presence of an aprotic solvent.

Preferably, the solvent for each of embodiments (1) to (6) is selected from:

for embodiment (1): aprotic solvents (e.g. from acetonitrile, N-methyl-2-pyrrolidone, dimethylformamide, dimethylacetamide, dimethyl sulfoxide and acetone);

for embodiment (2) in instances other than where both L groups together form the group —O—C(O)— or at least one of the L groups is selected from —OH, and embodiments (3) and (6): aprotic solvents (e.g. from tetrahydrofuran, acetonitrile, N-methyl-2-pyrrolidone, dimethylformamide, dimethylacetamide, dimethyl sulfoxide and acetone) and chlorinated solvents (e.g. from dichloromethane, dichloroethane and chloroform);

for embodiment (2) in instances in which both L groups together form the group —O—C(O)—O— or at least one of the L groups is selected from —OH: aprotic solvents (e.g. from N-methyl-2-pyrrolidone, dimethylformamide and acetonitrile) and, though less preferred, water (preferably at a pH of from 8.5-9.5, e.g. due to its use with a base such as ammonia);

for embodiment (4): aprotic solvents (e.g. from tetrahydrofuran, dimethoxyethane and dioxane); and for embodiment (5): aprotic solvents (e.g. from tetrahydrofuran, acetonitrile, N-methyl-2-pyrrolidone, dimethylformamide, dimethylacetamide, dimethyl sulfoxide, acetone and dioxane).

Step (i) may be carried out at a temperature of greater than 40° C., preferably greater than 50° C., and more preferably at a temperature of from 60 to 350° C. In some instances, the reaction is carried out under reflux. However, in embodiment (4), the reaction may be carried out at room temperature e.g. at a temperature at least 15° C., and preferably from 18 to 30° C.

Step (i) will generally be carried out at ambient pressure, i.e. approximately 1 bar, though higher pressures may be used. For instance, in embodiment (4), the reaction may be carried out at a pressure of greater than 2 bar, e.g. from 2 to 200 bar.

The reaction may be conducted for a period of greater than 30 minutes, but preferably less than 6 hours, and more preferably less than 4 hours. Longer reaction periods may also be used, such as up to 48 hours or even longer.

In embodiment (2) in instances in which both L groups together form the group —O—C(O)—O— or at least one of the L groups is selected from —OH, and in embodiment (4), a preferred method for preparing intermediate c involves carrying out step (i) in the presence of a base. Suitable bases may be selected from:

- inorganic bases, e.g. alkali metal hydroxides (such as sodium hydroxide and potassium hydroxides), alkali metal alkoxides (e.g. alkali metal tert-butoxides such as sodium tert-butoxide or potassium tert-butoxide), and alkali metal carbonates (such as sodium hydrogencarbonate, sodium carbonate, potassium hydrogencarbonate and potassium carbonate), and
- organic bases, e.g. nitrogen-containing organic bases, such as from tetra-n-butylammonium fluoride, trimethylamine, diisopropylethylamine, 1,8-diazabicyclo[5.4.0]undec-7-ene, pyridine and 4-dimethylaminopyridine.

The base is preferably an inorganic base and more preferably is a carbonate, in particular potassium carbonate.

The base may be used in an amount of from 0.005 to 0.3 molar equivalents, preferably from 0.01 to 0.1 molar equivalents, and more preferably from 0.03 to 0.06 molar equivalents as compared to starting material a. It will be appreciated that these quantities mean that the base preferably acts as a catalyst, and is not being used up as a reagent in the reaction. The reaction will generally be carried out in the absence of a metal catalyst.

In these embodiments, the alkylating agent b will generally be used in an amount of from 0.8 to 1.3 molar equivalents, preferably from 0.9 to 1.1 molar equivalents, and more preferably from 1 to 1.02 molar equivalents, as compared to starting material a. Thus, the alkylating agent may be used effectively in just a stoichiometric or slightly over stoichiometric amount. This is believed to improve the purity of the intermediate c that is obtained.

In these embodiments, step (i) is preferably carried out in the presence of a solvent. Step (i) may also be carried out in the absence of a solvent, though this is less preferred since intermediate c requires special handling when not used in a solvent.

The solvent is preferably a protic solvent. Protic solvents are well-known in the art as solvents which are capable of donating protons. Protic solvents typically contain hydrogen atoms directly bound to a nitrogen or an oxygen.

Suitable protic solvents include water and alcohols. The alcohol may be selected from $C_{1-10}$, preferably from $C_{3-8}$, and more preferably from $C_{5-6}$, alcohols. Preferred alcohols have the formula $C_nH_{2n+1}OH$, though polyols such as diols and triols may also be used and have the formula $C_nH_{2n+2-m}(OH)_m$ with m preferably selected from 2 or 3 (e.g. ethylene or propylene glycol). Preferably, the protic solvent is an alcohol, more preferably cyclohexanol or 4-methyl-2-pentanol.

It may be desirable to use a mixture of solvents, e.g. a mixture of two or more of the protic solvents described above. This can be useful where it is desirable to carry the reaction in a specific solvent boiling range. For instance, the reaction may be carried out in the presence of two or more alcohols, e.g. selected from $C_{3-8}$ alcohols, and more preferably from $C_{5-6}$ alcohols. In particular embodiments, the reaction is carried out in the presence of a mixture of isomers, e.g. a mixture of 4-methyl-2-pentanol and cyclohexanol.

Where a mixture of solvents is used, each solvent is preferably present in an amount of at least 10%, and preferably at least 15% by total weight of the solvent system. For instance, a mixture of 70-90% 4-methyl-2-pentanol and 10-30% cyclohexanol may be used.

The solvent may be used in an amount of from 1.5 to 8 g, preferably from 2 to 6 g, and more preferably from 2.5 to 4.0 g of solvent per g of starting material a.

In these embodiments, the reaction may be carried out at a temperature of at least 100° C., for instance at a temperature of from 100 to 180° C., preferably from 110 to 160° C., and more preferably at a temperature of from 120 to 150° C. In some instances, the reaction is carried out under reflux.

In these embodiments, the reaction will generally be carried out at ambient pressure, i.e. approximately 1 bar.

In these embodiments, the reaction may be conducted for a period of greater than 4 hours, but preferably less than 48 hours.

These embodiments are preferred since they are halogen-free. Particularly preferred alkylating agents b are those in which L and L' together form the group —O—C(O)—O—, i.e. organic carbonates, such as ethylene carbonate.

In step (ii) of the method, the intermediate c is subjected to a ring closing reaction to form fuel additive e:

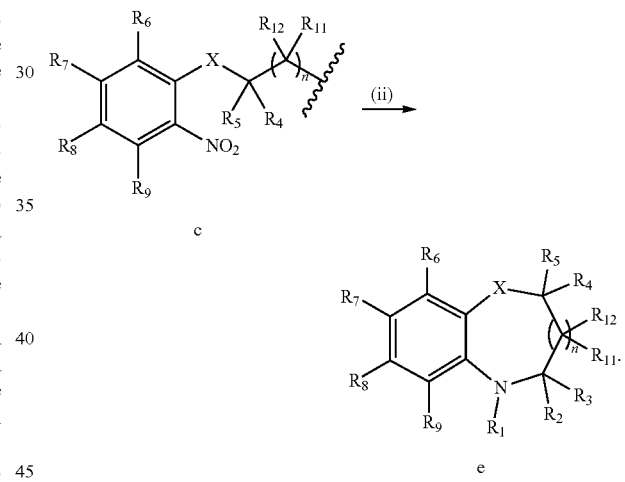

Step (ii) is preferably carried out in the presence of a hydrogenation catalyst and a hydrogen source. These conditions reduce the nitro group to an amine, thereby allowing ring closing to take place.

The hydrogenation catalyst is preferably selected from palladium, platinum, nickel (e.g. Raney nickel) and rhodium catalysts, though other metal catalysts may also be used such as vanadium. Preferred catalysts are generally selected from palladium and platinum catalysts, such as from Pd/C, Pt(OH)$_2$ and PtO$_2$. However, palladium and rhodium catalysts are particularly suitable in embodiment (1).

The hydrogen source in step (ii) is preferably hydrogen gas, for instance at a pressure of from 1 to 80 bar, preferably from 5 to 70 bar, and more preferably from 10 to 60 bar. Though less preferred, step (ii) may also be carried out using a hydrogen source other than hydrogen gas, such as hydrides, e.g. sodium borohydride, sodium bis(2-methoxyethoxy)aluminium hydride (known as 'Red-Al'), lithium aluminium hydride, diisobutylaluminium hydride, lithium borohydride or zinc borohydride.

Step (ii) is preferably carried out at a temperature of at least 20° C., for instance at a temperature of from 20 to 70° C., and preferably from 25 to 60° C.

Preferably, step (ii) is carried out in the presence of a protic solvent, such as an alcohol (e.g. methanol or ethanol) or an organic acid (e.g. acetic acid, optionally in the presence of an inorganic acetate salt, such as sodium acetate). These components are believed to maximise the activity of the catalyst.

Step (ii) is preferably carried out in the presence of a reaction additive. Preferably, the reaction additive is an acid, such as an acid selected from inorganic acids, such as hydrochloric acid, and organic acids, such as p-toluenesulfonic acid and acetic acid (acetic acid may also be used as the solvent). However, the reaction additive may also be ammonia, preferably used in combination with an alcohol such as methanol. The ammonia is preferably used in an amount of from 2 to 4 molar equivalents as compared to intermediate c. The use of ammonia as a reaction additive is particularly suitable for embodiment (1).

Step (ii) may also be carried out in the presence of catalysts other than those listed above, such as in the presence of sodium sulfide (e.g. preferably with alcohol solvent such as ethanol) and iron catalysts (preferably with an organic acid solvent such as acetic acid).

The reaction in step (ii) may be conducted for a period of greater than 1 hour, preferably greater than 2 hours. Typically the reaction will be carried out for up to 24 hours.

In some embodiments, step (ii) is carried out as a single reaction (i.e. with one set of reagents and under one set of conditions). However, in other embodiments, step (ii) comprises sub-steps.

Typically, in embodiments (1), (2) other than where both L groups together form the group —O—C(O)—O— or where at least one of the L groups is selected from —OH, (3) and (6), step (ii) may be carried out as a single reaction. The intermediate in embodiment (1) is particularly suited to single step reduction and cyclisation to form fuel additive e.

However, in embodiment (3), step (ii) may also comprise sub-steps. Preferably, the conditions for one of the sub-steps are as described above for step (ii) (i.e. the reaction is preferably conducted in the presence of a hydrogenation catalyst and a hydrogen source), and the other of sub-steps comprises hydrolysing the acetal group, e.g. using an acid, to form an aldehyde. Where hydrolysis is carried out first, then intermediate c of embodiment (6) will be formed. By reducing the nitro group and hydrolysing the acetal, ring closing may then occur.

Hydrolysis may be carried out in the presence of an acid, e.g. a hydrogen halide such as HCl. Preferably the acid will be used as an aqueous acid. Suitable solvents for the hydrolysis reaction include aprotic solvents (e.g. acetone and acetonitrile). Hydrolysis may take place at a temperature of greater than 40° C., e.g. from 40 to 90° C. and preferably from 50 to 80° C. Hydrolysis will typically take place at room temperature. Hydrolysis may take place for greater than 2 hours, e.g. from 4 to 48 hours.

In embodiments (2) where both L groups together form the group —O—C(O)— or where at least one of the L groups is selected from —OH, (4) and (5), step (ii) will preferably comprise sub-steps to improve the conversion of intermediate c to fuel additive e.

In embodiments in which intermediate c comprises a terminal hydroxy group (i.e. embodiment (2) where both L groups together form the group —O—C(O)— or at least one of the L groups is selected from —OH and embodiment (4)), step (ii) preferably comprises sub-steps (iia) and (iib), where the conditions for one of sub-steps (iia) and (iib) are as described above for step (ii) (i.e. the reaction is preferably conducted in the presence of a hydrogenation catalyst and a hydrogen source), and the other of sub-steps (iia) and (iib) comprises replacing the hydroxyl group with a leaving group L" which is selected from halogens (e.g. Cl, Br, I, preferably Cl or Br, and more preferably Br) and sulfonates (e.g. —OSO$_2$A, where A is selected from tolyl, methyl, —CF$_3$, —CH$_2$Cl, phenyl and p-nitrophenyl) in a substitution reaction. Since halogens and sulfonates are better leaving groups than hydroxy groups, this encourages ring formation.

Where the substitution reaction is a halogenation reaction, it may be conducted in the presence of a hydrogen halide, preferably hydrogen bromide or hydrogen chloride.

The hydrogen halide is preferably in the form of an aqueous solution.

A molar excess of hydrogen halide is preferably used, for instance by using a molar ratio of hydrogen halide to intermediate c of at least 5:1, preferably at least 10:1, and more preferably at least 15:1.

The halogenation reaction may be conducted at a temperature of greater than 60° C., preferably greater than 70° C., and more preferably greater than 80° C.

The substitution reaction will generally be carried out at ambient pressure, i.e. approximately 1 bar.

The substitution reaction may be conducted for a period of greater than 1 hour, preferably greater than 2 hours.

Alternatively, the halogenation reaction may be conducted in the presence of a thionyl halide, a phosphorus tetrahalide, a phosphorus pentahalide, a phosphoryl halide, or halogen gas (i.e. Br$_2$, Cl$_2$, etc.) or a carbon tetrahalide in combination with a trialkylphosphine (e.g. trimethyl phosphine) or a triaryl phosphine (e.g. triphenyl phosphine). In these embodiments, the halogenation reaction is preferably conducted in the presence of an aprotic solvent (e.g. tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane or propionitrile, and preferably a non-ether aprotic solvent, such as dimethyl formamide, N-methyl-2-pyrrolidone, dimethylformamide, dimethylacetamide, dimethyl sulfoxide, acetone, dioxane, ethylene carbonate and acetonitrile) or a chlorinated solvent (e.g. dichloromethane, dichloroethylene or trichloromethane).

For instance, the halogenation reaction may be carried out using: a thionyl halide, in the presence of a chlorinated solvent (e.g. dichloromethane, dichloroethylene or trichloromethane); a halogen gas or carbon tetrahalide in the presence of a triaryl phosphine (e.g. triphenyl phosphine) or trialkyl phosphine and preferably an aprotic solvent (e.g. acetonitrile) or a chlorinated solvent (e.g. dichloromethane); a phosphorus trihalide, a phosphorus pentahalide or a phosphoryl halide, preferably in the presence of an ammonium salt (e.g. tetraalkylammonium halides such as tetrabutylammonium bromide); or an alkyl- or aryl-sulfonyl chloride (e.g. toluenesulfonyl chloride or methanesulfonyl chloride), preferably in the presence of a trialkylamine (e.g. trimethyl amine), and preferably in the presence of a chlorinated solvent (e.g. dichloromethane).

Where the terminal hydroxyl group is substituted with a sulfonate group, the reaction may be carried out using HalOSO$_2$A or ASO$_2$—O—SO$_2$A, where Hal is a halogen (preferably selected from Cl and Br) and A is selected from tolyl, methyl, —CF₃, —CH₂Cl, phenyl and p-nitrophenyl. The reaction may be conducted in the presence of an aprotic solvent (e.g. tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane or propionitrile, and preferably a non-ether aprotic solvent, such as dimethyl formamide, N-methyl-2-pyrrolidone, dimethylformamide, dimethylacetamide, dimethyl sulfoxide, acetone, dioxane, ethylene carbonate or acetonitrile, and preferably dimethyl formamide, N-methyl-2-pyrrolidone, dimethylformamide, dimethylacetamide, dimethyl sulfoxide, acetone, dioxane, ethylene carbonate or acetonitrile) or a chlorinated solvent (e.g. dichloromethane, dichloroethylene or trichloromethane).

Where L" is a sulfonate, the substitution reaction preferably takes place in step (iia).

In other, particularly preferred, embodiments in which intermediate c comprises a terminal hydroxy group, the ring closing reaction may proceed via a two-step metal-catalysed mechanism, in which the nitro group is first reduced to an amine in step (iia"), thereby allowing ring closing to take place in step (iib"):

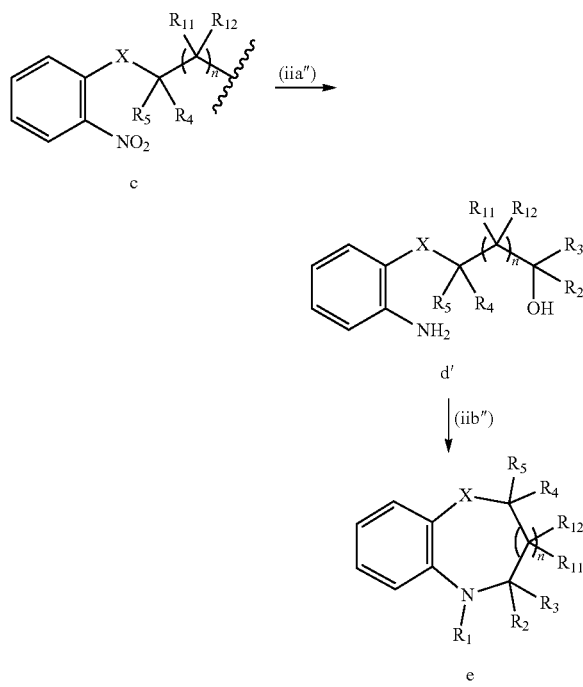

The same metal catalyst may be used in steps (iia") and (iib") of the reaction, thereby enabling the reaction to be carried out in one pot.

At least step (iia") is carried out in the presence of a hydrogen source. At least step (iib") is carried out at a temperature of at least 100° C. and preferably in the presence of an aprotic solvent system.

The reaction is preferably carried out as a one-step reaction in which the same reaction materials, and preferably the same reaction conditions, are used in steps (iia") and (iib"). Thus, the reaction is preferably carried out as a single step reaction, even though it proceeds via a two-step mechanism. In other, less preferred, embodiments, the reaction may be carried out as a two-step reaction in which a first set of reaction materials and conditions are used to reduce the nitro group in step (iia"), and a second set of reaction materials and conditions are used to close the ring in step (iib").

An advantage of metal-catalysed ring closing reaction is that it does not require the use of reagents in stoichiometric amounts. In preferred embodiments, no reagents beyond intermediate c and the hydrogen source are used. Intermediate c and the hydrogen source are considered to be reagents because they are consumed in the course of the reaction. The other components used in the reaction, such as the metal catalyst, are not considered to be 'reagents' since they are not consumed in the course of the reaction. In embodiments, each of the components used in the reaction, aside from intermediate c, the hydrogen source, and the aprotic solvent system, are used in amount of up to 0.5 molar equivalents, preferably up to 0.3 molar equivalents, and more preferably up to 0.2 molar equivalents, as compared to intermediate c.

The metal-catalysed ring closing reaction is preferably carried out in the absence of halogen-containing reagents and acidic reagents, preferably strongly acidic reagents (i.e. compounds which have a pH of less than 5 at 25° C. when present as a 0.01M aqueous solution of said compound).

Preferably, the reaction is carried out using intermediate c as the reagent only in the presence of a metal catalyst, hydrogen source and solvent system, i.e. no further reaction materials are used.

Specific routes by which the fuel additive e may be prepared via a metal-catalysed reaction will now be detailed.

(1) One-Step Reaction

In preferred embodiments, the reaction is preferably carried out as a one-step reaction. Thus, the same reaction materials are used in steps (iia") and (iib"), i.e. steps (iia") and (iib") are carried out in the presence of a metal catalyst, a hydrogen source and an aprotic solvent system.

It will be appreciated that metal catalysts are metal-containing catalysts and, as such, they may contain non-metallic elements. Suitable metal catalysts for use in the one-step metal-catalysed reaction include those selected from palladium (e.g. Pd/C), nickel (e.g. in the presence of aluminium such as in Raney nickel or Ni—SiO₂/Al₂O₃) and cobalt (e.g. in the presence of aluminium such as in Raney cobalt) catalysts. Nickel catalysts, in particular Ni—SiO₂/Al₂O₃, are particularly preferred.

The metal catalyst may be used in an amount of up to 0.3 molar equivalents, for instance from 0.005 to 0.3 molar equivalents, preferably from 0.01 to 0.25 molar equivalents, and more preferably from 0.05 to 0.2 molar equivalents, as compared to intermediate c.

The reaction is also carried out in the presence of a hydrogen source. The hydrogen source is preferably hydrogen gas, for instance at a pressure of from 1 to 50 bar, preferably from 3 to 30 bar, and more preferably from 5 to 15 bar.

Though less preferred, hydrogen transfer reagents could also be used as the hydrogen source, e.g. formic acid, sodium formate or ammonium formate. Hydrogen transfer reagents generate hydrogen gas in-situ. Hydrogen transfer reagents may be used in combination with hydrogen gas, or as the sole hydrogen source. Hydrogen transfer reagents are preferably used in combination with palladium catalysts, such as Pd/C.

Hydrogen transfer reagents may be used in an amount of to 5 molar equivalents, for instance from 0.1 to 5 molar equivalents, preferably from 0.5 to 4 molar equivalents, and more preferably from 1 to 3 molar equivalents, as compared to intermediate c.

The one-step reaction is carried out in the presence of an aprotic solvent system. The aprotic solvent system is believed to favour the removal of water from the reaction mixture, particularly at reflux, which encourages the oxidative cyclisation to proceed.

It will be appreciated that an aprotic solvent system is substantially free from any protic solvents, i.e. contains less than 2% by volume, preferably less than 1% by volume, and more preferably less than 0.1% by volume of protic solvents.

The aprotic solvent system preferably comprises an aromatic solvent, such as a solvent selected from toluene, benzene, xylenes, trimethyl benzenes such as mesitylene, diphenyl ether, naphthalene, methyl-substituted naphthalenes (i.e. 1- or 2-methylnaphthalene) and anisole. Mesitylene is particularly suited for the one-step metal catalysed reaction, delivering high yields of the fuel additive e. A refinery stream containing a mixture of aromatic compounds with a suitable boiling range (e.g. falling within the range of 100 to 250° C.) may also be used.

The aromatic solvent may be present in the aprotic solvent system in an amount of at least 30%, preferably at least 40%, and more preferably at least 50%, by weight. In embodiments, the aromatic solvent is the only solvent that is used, i.e. the aprotic solvent system consists of the aromatic solvent.

The aprotic solvent system may also comprise a non-aromatic solvent. Preferred non-aromatic solvents are selected from heterocyclic solvents, such as from tetrahydrofuran and 1,4-dioxane. Other suitable aprotic non-aromatic solvents include dimethylacetamide. The non-aromatic solvent is preferably used in combination with an aromatic solvent.

Where the reaction is carried out as a one-step reaction, the reaction conditions are preferably the same in both steps (iia") and (iib"), i.e. steps (iia") and (iib") are carried out at a temperature of at least 100° C. In some embodiments, pressure may be required to maintain the solvent system in the liquid phase at a temperature of greater than 100° C. This may be the case where, for instance, benzene or tetrahydrofuran is used. Suitable pressures may be achieved by carrying out the reaction in the presence of hydrogen gas at the pressures given above, or further pressure may be applied beyond that conferred by the hydrogen gas.

Preferably, steps (iia") and (iib") are carried out, for instance at a temperature of from 100 to 250° C., preferably from 120 to 200° C., and more preferably from 130 to 180° C. The one-step reaction is preferably carried out under reflux.

In some embodiments, the method comprises a pre-heating step which is carried out before step (iia"). During the pre-heating step, the reaction may be brought up to temperature over a period of up to 3 hours, preferably up to 2 hours, and more preferably up to 1.5 hours. The pre-heating step may be carried out at a temperature of from 40 to 100° C.

The one-step reaction (i.e. steps (iia") and (iib") together) may be conducted for a period of greater than 2 hours, preferably greater than 4 hours. Typically, the one-step reaction will be carried out for up to 24 hours. These values do not include any time periods during which the reaction mixture is pre-heated.

(2) Two-Step Reaction

The metal-catalysed ring closing reaction may also be carried out as a two-step reaction in which different reaction materials, and preferably different conditions, are used in steps (iia") and (iib"). Although different reaction materials may be used in steps (iia") and (iib"), the same metal catalyst may be used throughout. This enables the reaction to be carried out as a one-pot reaction.

Suitable metal catalysts for use in the two-step, but preferably one-pot, reaction include those selected from palladium (e.g. Pd/C), nickel (e.g. in the presence of aluminium such as in Raney nickel or Ni—$SiO_2/Al_2O_3$), cobalt (e.g. in the presence of aluminium such as in Raney cobalt). Nickel catalysts, in particular Raney-nickel, and palladium catalysts, in particular Pd/C, are particularly preferred.

The metal catalyst may be used in an amount of up to 0.3 molar equivalents, for instance from 0.005 to 0.3 molar equivalents, preferably from 0.01 to 0.25 molar equivalents, and more preferably from 0.05 to 0.2 molar equivalents, as compared to intermediate c.

Typically, all of the catalyst will be added at the beginning of step (iia"). However, in some embodiments, it may be desirable to add some of the metal catalyst at the beginning of step (iia") and the rest of the metal catalyst at a later time in the reaction, e.g. at the beginning of step (iib"). In these embodiment, higher quantities of metal catalyst as compared to intermediate c may be used, for instance from 0.005 to 0.3 molar equivalents, preferably from 0.01 to 0.25 molar equivalents, and more preferably from 0.05 to 0.2 molar equivalents, in step (iia") and from 0.005 to 0.3 further molar equivalents, preferably from 0.01 to 0.25 further molar equivalents, and more preferably from 0.05 to 0.2 further molar equivalents, in step (iib").

Step (iia") of the two-step reaction is carried out in the presence of a hydrogen source. The hydrogen source is preferably hydrogen gas, for instance at a pressure of from 1 to 50 bar, preferably from 3 to 30 bar, and more preferably from 5 to 15 bar.

Though less preferred, hydrogen transfer reagents could also be used as the hydrogen source, e.g. formic acid, sodium formate or ammonium formate. Hydrogen transfer reagents generate hydrogen gas in-situ. Hydrogen transfer reagents may be used in combination with hydrogen gas, or as the sole hydrogen source. Hydrogen transfer reagents are preferably used in combination with palladium catalysts, such as Pd/C.

Hydrogen transfer reagents may be used in an amount of to 5 molar equivalents, for instance from 0.1 to 5 molar equivalents, preferably from 0.5 to 4 molar equivalents, and more preferably from 1 to 3 molar equivalents, as compared to intermediate c.

Step (iib") of the two-step reaction may also be carried out in the presence of a hydrogen source, e.g. as described in relation to step (iia"). For instance, step (iib") may be carried out in the presence of the same hydrogen source as step (iia"). However, step (iib") may also be carried out in the absence of a hydrogen source. For instance, the reaction chamber may be ventilated to remove any hydrogen gas before step (iib"). In this case, step (iib") is preferably carried out at ambient pressure, i.e. at a pressure of approximately 1 bar.

Step (iib") of the two-step reaction is preferably carried out in the presence of an aprotic solvent system. The aprotic solvent system is believed to favour the removal of water from the reaction mixture, particularly at reflux, which encourages the oxidative cyclisation to proceed.

The aprotic solvent system preferably comprises an aromatic solvent, such as a solvent selected from toluene, benzene, xylenes, trimethyl benzenes such as mesitylene, diphenyl ether, naphthalene, methyl-substituted naphthalenes and anisole. Mesitylene is particularly suited to the method of the present invention, delivering high yields of the fuel additive e. A refinery stream containing a mixture of aromatic compounds with a suitable boiling range (e.g. falling within the range of 100 to 250° C.) may also be used.

The aromatic solvent may be present in the aprotic solvent system in an amount of at least 30%, preferably at least 40%, and more preferably at least 50%, by weight. In embodiments, the aromatic solvent is the only solvent that is used, i.e. the aprotic solvent system consists of the aromatic solvent.

The aprotic solvent system may also comprise a non-aromatic solvent. Preferred non-aromatic solvents are selected from heterocyclic solvents, such as from tetrahydrofuran and 1,4-dioxane. The non-aromatic solvent is preferably used in combination with an aromatic solvent.

Step (iia") of the two-step reaction is preferably also carried out in the presence of an aprotic solvent system, e.g. as described above, as this is believed to give higher yields. However, it may also be carried out in the presence of a protic solvent system, such as aqueous, i.e. water-containing, solvent systems or alcohol solvent systems (e.g. methanol or ethanol).

Where the reaction is carried out as a two-step reaction, the reaction conditions are preferably different in both steps (iia") and (iib"). Step (iib") is carried out at a temperature of at least 100° C. As mentioned above, pressure may be required to maintain the solvent system in the liquid phase at a temperature of greater than 100° C. Suitable pressures may be achieved by carrying out the reaction in the presence of hydrogen gas at the pressures given above, or further pressure may be applied beyond that conferred by the hydrogen gas.

Step (iib") is preferably carried out for, for instance at a temperature of from 100 to 250° C., preferably from 120 to 200° C., and more preferably from 130 to 180° C. Step (iib") is preferably carried out under reflux.

However, step (iia") is preferably carried out at a lower temperature than step (iib"). For instance, step (iia") may be carried out at a temperature of from 10 to 100° C., preferably 15 to 80° C., and more preferably from 20 to 60° C.

The two-step reaction (i.e. steps (iia") and (iib") together) may be conducted for a period of greater than 2 hours, preferably greater than 10 hours. Step (iia") is preferably carried out for a period of greater than 1 hour. Step (iib") is preferably carried out for a period of greater than 8 hours. Typically, the two-step reaction (i.e. steps (iia") and (iib") together) will be carried out for up to 48 hours.

In embodiment (5), intermediate c comprises a terminal acid or ester group. In these embodiments, step (ii) preferably comprises the following sub-steps:

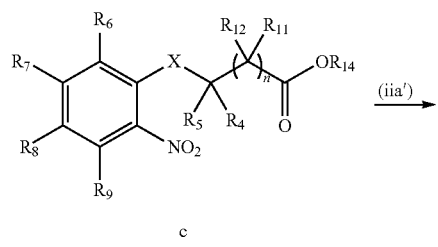

c

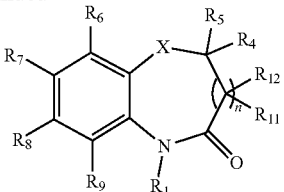

d (iib')

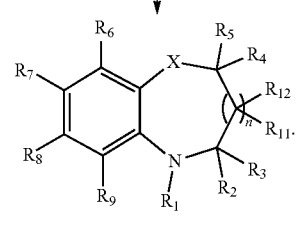

e

The conditions for sub-step (iia') are as described above for step (ii), i.e. the reaction is preferably conducted in the presence of a hydrogenation catalyst and a hydrogen source. This leads to the formation of an intermediate d which comprises an amide. Sub-step (iib') comprises reducing the amide to an amine.

Reduction of the amide to an amine may be carried out in the presence of a reducing agent or using catalytic reduction.

Preferred reducing agents for use in sub-step (iib') are selected from sodium bis(2-methoxyethoxy)aluminumhydride (known as 'Red-Al'), lithium aluminium hydride, borane (preferably in combination with dimethyl sulfide), diisobutylaluminium hydride, and borohydrides. Suitable borohydrides include: sodium borohydride, preferably in combination with boron trifluoride diethyl etherate, iodine, titanium tetrachloride, cobalt (II) chloride or acetic acid; lithium borohydride, preferably in combination with trimethylsilyl chloride; and zinc borohydride.

Where Red-Al is used, this is preferably in combination with an alkali metal halide, such as potassium fluoride. The alkali metal halide may be used in an amount of from 0.1 to 1%, preferably from 0.2 to 0.6% by weight of intermediate d.

The reducing agent may be added dropwise to the reaction mixture, e.g. over a period of at least 2 hours, preferably at least 3 hours, and more preferably at least 4 hours.

The reducing agent may be used in sub-step (iib') in an amount of from 1 to 4 molar equivalents, preferably from 1.5 to 3 molar equivalents, and more preferably from 1.75 to 2.25 molar equivalents, as compared to intermediate d.

An aprotic solvent is preferably used with the reducing agent, for instance an aprotic solvent selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile, and preferably from toluene, tetrahydrofuran, dimethoxyethane and dioxane. In some embodiments, tetrahydrofuran is preferred for use as the aprotic solvent.

The aprotic solvent may be used in step (iib') an amount of from 4 to 20 equivalents, preferably from 6 to 16 equivalents, and more preferably from 8 to 12 equivalents by weight relative to intermediate d.

Preferred combinations of reducing agent/solvent are as follows:

Red-Al/toluene lithium aluminium hydride/tetrahydrofuran or dimethoxyethane or dioxane borane, in combination with dimethyl sulfide/tetrahydrofuran diisobutylaluminium hydride/tetrahydrofuran sodium borohydride, boron trifluoride diethyl etherate/tetrahydrofuran sodium borohydride, iodine/tetrahydrofuran lithium borohydride, trimethylsilyl chloride/tetrahydrofuran sodium borohydride, titanium tetrachloride/dimethoxyethane zinc borohydride/tetrahydrofuran sodium borohydride, cobalt (II) chloride/tetrahydrofuran sodium borohydride, acetic acid/dioxane Where step (iib') is carried out in the presence of a reducing agent, it is preferably carried out at ambient temperature (i.e. at a temperature of from 15 to 25° C.). Since the reaction may be exothermic, the reaction mixture may require cooling to maintain the temperature in this range. In other embodiments, the reaction may be cooled e.g. to a temperature of lower than 15° C., such as from 0 to 10° C.

The reaction is preferably carried out at ambient pressure, i.e. a pressure of approximately 1 bar.

Where step (iib') is carried out in the presence of a reducing agent, the reaction may be quenched using a base, preferably an inorganic base such as an alkali metal hydroxide. Sodium hydroxide and potassium hydroxide are preferred, particularly sodium hydroxide.

The base that is used for quenching may be added dropwise over a period of at least 30 minutes, preferably at least 1 hour, and more preferably at least 2 hours.

Where sub-step (iib') is carried out using catalytic reduction, it may be carried out in the presence of hydrogen at a pressure of from 1 to 80 bar, preferably from 3 to 60 bar, and more preferably from 5 to 50 bar.

Suitable catalysts for sub-step (iib') include ruthenium, platinum, palladium and rhodium catalysts, with ruthenium catalysts such as ruthenium (III) acetylacetonate preferred.

In some particularly preferred embodiments, a ruthenium hydrogenation catalyst may be formed in-situ from a mixture of ruthenium (III) acetylacetonate, a triphos (e.g. 1,1,1-tris(diphenylphosphinomethyl)ethane) and ytterbium (III) trifluoromethanesulfonate, preferably in the presence of methanesulfonic acid and trifluoromethanesulfonimide.

The catalyst may be used in an amount of less than 1 molar equivalent, preferably less than 0.5 molar equivalents, and more preferably less than 0.1 molar equivalents as compared to intermediate d.

Where step (iib') is carried out using catalytic reduction, an aprotic solvent is preferably used with the catalyst, for instance an aprotic solvent selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile. The aprotic solvent is preferably tetrahydrofuran.

Where step (iib') is carried out using catalytic reduction, the reaction may be conducted at a temperature of greater than 80° C., preferably greater than 100° C., and more preferably greater than 120° C.

The reaction in step (iib') is preferably conducted for at least 2 hours, preferably at least 5 hours and more preferably at least 10 hours.

In a very specific embodiment, step (iib') is carried out in the presence of a reducing agent (e.g. Red-Al), a solvent (e.g. toluene), and at a temperature of 10 to 20° C. The reaction is quenched using a base (e.g. sodium hydroxide).

In another very specific embodiment, step (iib') is carried out in the presence of a reducing agent (e.g. lithium aluminium hydride), a solvent (e.g. tetrahydrofuran) with the temperature maintained at below 10° C.

In another very specific embodiments, step (iib') is carried out in the presence of a reducing agent (e.g. borane), a solvent (e.g. tetrahydrofuran) and at a temperature of 0 to 5° C.

In other embodiments, where step (iib') is carried out using catalytic reduction, it may be carried out in the absence of hydrogen gas, e.g. hydrogen gas is present at a level of less than 10 ppm and preferably less than 1 ppm by volume. In these embodiments, the reaction is carried out in the presence of a silane hydrogen source. Suitable silanes include alkoxy silanes (e.g. $(EtO)_3SiH$) and aryl silanes (e.g. $PhSiH_3$).

Preferred catalysts for carrying out the reaction in the absence of hydrogen gas are selected from metal catalysts. Preferably the catalyst is selected from ruthenium and zinc catalysts. The catalyst may be used in an amount of up to 0.5 molar equivalents, preferably from 0.01 to 0.15 molar equivalents as compared to intermediate d.

Where step (iib') is carried out using catalytic reduction but in the absence of hydrogen gas, step (iib') is preferably conducted in the presence of a solvent, preferably selected from aprotic solvents such as those listed previously in connection with step (iib'), and is preferably tetrahydrofuran.

Where step (iib') is carried out using catalytic reduction but in the absence of hydrogen gas, step (iib') may be conducted at a temperature of greater than 10° C., preferably from 15 to 50° C., and more preferably from 20 to 40° C.

Where step (iib') is carried out using catalytic reduction but in the absence of hydrogen gas, step (iib') may be conducted at ambient pressure, i.e. approximately 1 bar. The reaction may be carried out under an inert atmosphere, e.g. an under argon.

Where step (iib') is carried out using catalytic reduction but in the absence of hydrogen gas, the reaction may be conducted for a period of greater than 20 minutes, preferably greater than 1 hour, but preferably less than 24 hours.

The methods of the present invention are preferably carried out on an industrial scale. For instance, where the method of preparing fuel additive e is a batch process, the fuel additive e is preferably produced in a batch quantity of greater than 100 kg, preferably greater than 150 kg, and more preferably greater than 200 kg. The method may also be carried out as a continuous process.

In order to produce the fuel additive on an industrial scale, steps (i) and (ii) are preferably carried out in reactors having a capacity of at least 500 L, preferably at least 750 L, and more preferably at least 1000 L. It will be appreciated that both steps (i) and (ii) may be carried out in the same reactor.

Octane-Boosting Fuel Additive e

Fuel additives e that are prepared using the methods of the present invention have the following formula:

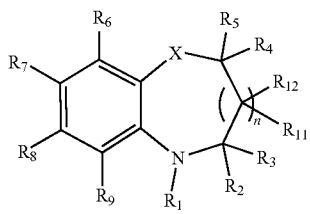

where: R$_1$ is hydrogen;

R$_2$, R$_3$, R$_4$, R$_5$, R$_{11}$ and R$_{12}$ are each independently selected from hydrogen, alkyl, alkoxy, alkoxy-alkyl, secondary amine and tertiary amine groups;

R$_6$, R$_7$, R$_8$ and R$_9$ are each independently selected from hydrogen, alkyl, alkoxy, alkoxy-alkyl, secondary amine and tertiary amine groups;

X is selected from —O— or —NR$_{10}$—, where R$_{10}$ is selected from hydrogen and alkyl groups; and n is 0 or 1.

Preferred substituents for the fuel additives are described below. It will be appreciated that the preferred substitution patterns also apply to the starting material a, reagent b, and intermediates c, d and d' from which the fuel additive e is prepared.

In some embodiments, R$_2$, R$_3$, R$_4$, R$_5$, R$_{11}$ and R$_{12}$ are each independently selected from hydrogen and alkyl groups, and preferably from hydrogen, methyl, ethyl, propyl and butyl groups. More preferably, R$_2$, R$_3$, R$_4$, R$_5$, R$_{11}$ and R$_{12}$ are each independently selected from hydrogen, methyl and ethyl, and even more preferably from hydrogen and methyl.

In some embodiments, R$_6$, R$_7$, R$_8$ and R$_9$ are each independently selected from hydrogen, alkyl and alkoxy groups, and preferably from hydrogen, methyl, ethyl, propyl, butyl, methoxy, ethoxy and propoxy groups. More preferably, R$_6$, R$_7$, R$_8$ and R$_9$ are each independently selected from hydrogen, methyl, ethyl and methoxy, and even more preferably from hydrogen, methyl and methoxy.

Advantageously, at least one of R$_2$, R$_3$, R$_4$, R$_5$, R$_6$, R$_7$, R$_8$, R$_9$, R$_{11}$ and R$_{12}$, and preferably at least one of R$_6$, R$_7$, R$_8$ and R$_9$, is selected from a group other than hydrogen. More preferably, at least one of R$_7$ and R$_8$ is selected from a group other than hydrogen.

Alternatively stated, the octane-boosting additive may be substituted in at least one of the positions represented by R$_2$, R$_3$, R$_4$, R$_5$, R$_6$, R$_7$, R$_8$, R$_9$, R$_{11}$ and R$_{12}$, preferably in at least one of the positions represented by R$_6$, R$_7$, R$_8$ and R$_9$, and more preferably in at least one of the positions represented by R$_7$ and R$_8$. It is believed that the presence of at least one group other than hydrogen may improve the solubility of the octane-boosting additives in a fuel.

Also advantageously, no more than five, preferably no more than three, and more preferably no more than two, of R$_2$, R$_3$, R$_4$, R$_5$, R$_6$, R$_7$, R$_8$, R$_9$, R$_{11}$ and R$_{12}$ are selected from a group other than hydrogen. Preferably, one or two of R$_2$, R$_3$, R$_4$, R$_5$, R$_6$, R$_7$, R$_8$, R$_9$, R$_{11}$ and R$_{12}$ are selected from a group other than hydrogen. In some embodiments, only one of R$_2$, R$_3$, R$_4$, R$_5$, R$_6$, R$_7$, R$_8$, R$_9$, R$_{11}$ and R$_{12}$ is selected from a group other than hydrogen.

It is also preferred that at least one of R$_2$ and R$_3$ is hydrogen, and more preferred that both of R$_2$ and R$_3$ are hydrogen.

In preferred embodiments, at least one of R$_4$, R$_5$, R$_7$ and R$_8$ is selected from methyl, ethyl, propyl and butyl groups and the remainder of R$_2$, R$_3$, R$_4$, R$_5$, R$_6$, R$_7$, R$_8$, R$_9$, R$_{11}$ and R$_{12}$ are hydrogen. More preferably, at least one of R$_7$ and R$_8$ are selected from methyl, ethyl, propyl and butyl groups and the remainder of R$_2$, R$_3$, R$_4$, R$_5$, R$_6$, R$_7$, R$_8$, R$_9$, R$_{11}$ and R$_{12}$ are hydrogen.

In further preferred embodiments, at least one of R$_4$, R$_5$, R$_7$ and R$_8$ is a methyl group and the remainder of R$_2$, R$_3$, R$_4$, R$_5$, R$_6$, R$_7$, R$_8$, R$_9$, R$_{11}$ and R$_{12}$ are hydrogen. More preferably, at least one of R$_7$ and R$_8$ is a methyl group and the remainder of R$_2$, R$_3$, R$_4$, R$_5$, R$_6$, R$_7$, R$_8$, R$_9$, R$_{11}$ and R$_{12}$ are hydrogen.

Preferably, X is —O— or —NR$_{10}$—, where R$_{10}$ is selected from hydrogen, methyl, ethyl, propyl and butyl groups, and preferably from hydrogen, methyl and ethyl groups. More preferably, R$_{10}$ is hydrogen. In preferred embodiments, X is —O—.

n may be 0 or 1, though it is preferred that n is 0.

Octane-boosting additives that may be used in the present invention include:

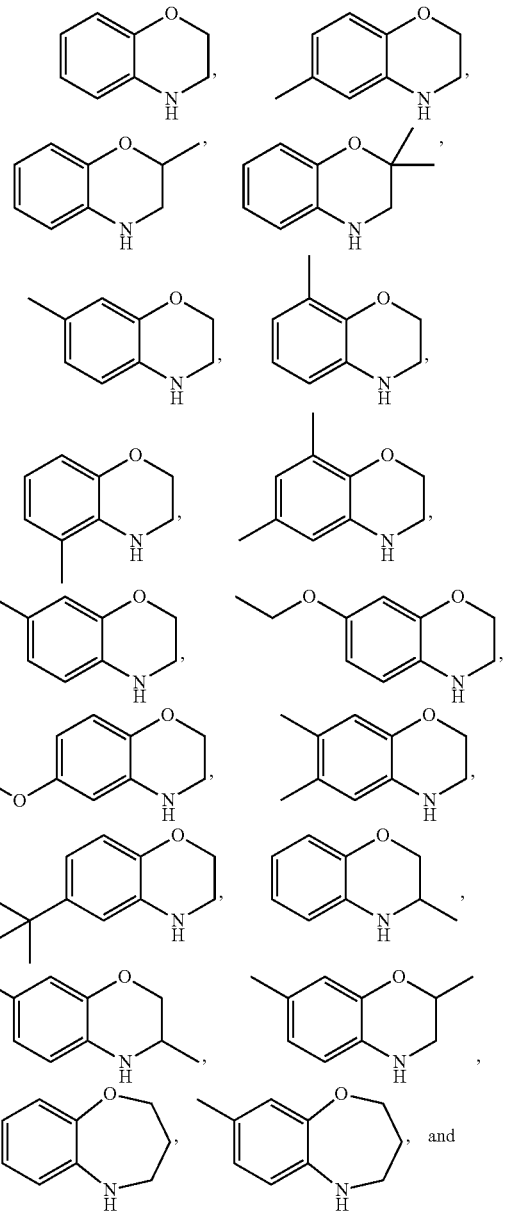

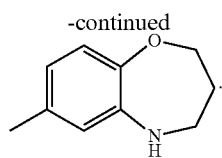

Preferred octane-boosting additives include:

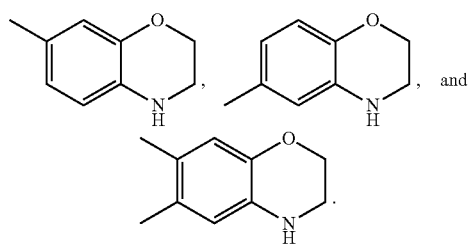

Particularly preferred is the octane-boosting additive:

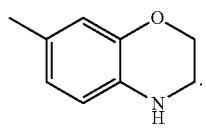

A mixture of fuel additives e may be used in the fuel composition. For instance, the fuel composition may comprise a mixture of:

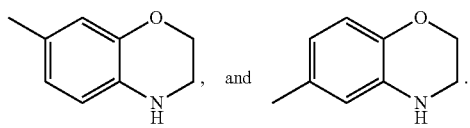

It will be appreciated that references to alkyl groups include different isomers of the alkyl group. For instance, references to propyl groups embrace n-propyl and i-propyl groups, and references to butyl embrace n-butyl, isobutyl, sec-butyl and tert-butyl groups.

Additive and Fuel Compositions

The present invention provides fuel additives e which are obtainable by a method of the present invention. Preferably, the fuel additives are obtained by a method of the present invention.

The present invention also provides a process for preparing a fuel for a spark-ignition internal combustion engine, said process comprising:

preparing a fuel additive e using a method of the present invention; and blending the fuel additive with a base fuel.

A fuel for a spark-ignition internal combustion engine is also provided. The fuel comprises a fuel additive e, obtainable and preferably obtained by a method of the present invention, and a base fuel.

Gasoline fuels (including those containing oxygenates) are typically used in spark-ignition internal combustion engines. Commensurately, the fuel composition that may be prepared according to the process of the present invention may be a gasoline fuel composition.

The fuel composition may comprise a major amount (i.e. greater than 50% by weight) of liquid fuel ("base fuel") and a minor amount (i.e. less than 50% by weight) of fuel additive composition of the present invention. Examples of suitable liquid fuels include hydrocarbon fuels, oxygenate fuels and combinations thereof.

The fuel composition may contain the octane-boosting fuel additive e in an amount of up to 20%, preferably from 0.1% to 10%, and more preferably from 0.2% to 5% weight additive/weight base fuel. Even more preferably, the fuel composition contains the fuel additive in an amount of from 0.25% to 2%, and even more preferably still from 0.3% to 1% weight additive/weight base fuel. It will be appreciated that, when more than one octane-boosting fuel additive e is used, these values refer to the total amount of octane-boosting additive described herein in the fuel.

The fuel compositions may comprise at least one other further fuel additive. Examples of such other additives that may be present in the fuel compositions include detergents, friction modifiers/anti-wear additives, corrosion inhibitors, combustion modifiers, anti-oxidants, valve seat recession additives, dehazers/demulsifiers, dyes, markers, odorants, anti-static agents, anti-microbial agents, and lubricity improvers. Further octane improvers may also be used in the fuel composition, i.e. octane improvers which do not have the structure of octane-boosting fuel additive e.

The fuel compositions are used in a spark-ignition internal combustion engine. Examples of spark-ignition internal combustion engines include direct injection spark-ignition engines and port fuel injection spark-ignition engines. The spark-ignition internal combustion engine may be used in automotive applications, e.g. in a vehicle such as a passenger car.

The invention will now be described with reference to the following non-limiting examples.

EXAMPLES

Example 1

Preparation of Fuel Additive e According to Embodiment (1)

In step (i), the following intermediate c was prepared using a variety of reagents b:

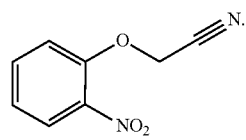 [SMILES: N#CCOc1ccccc1[N+](=O)[O-]]

In a first experiment, bromonitrile was used as reagent b. Specifically, 2-nitrophenol (10.0 g, 72 mmol), bromoacetonitrile (0.9 eq) and $K_2CO_3$ (2 eq) were refluxed in acetonitrile for 20 hours. The solvent was evaporated and the residue was partitioned between water and ethyl acetate, the organic layer washed three times with an aqueous solution of $K_2CO_3$. The organic phase was dried over sodium sulphate, the solvent was removed in vacuo and the residue was triturated with hexane to give 11.1 g (86% yield) of intermediate c as a light green solid.

In a second experiment, chloronitrile was used as reagent b. Specifically, 2-nitrophenol (10.0 g, 72 mmol), chloroacetonitrile (0.9 eq) and $K_2CO_3$ (2 eq) were refluxed in acetonitrile for 20 hours. The solvent was evaporated and the residue was partitioned between water and ethyl acetate. The organic layer was washed three times with an aqueous solution of $K_2CO_3$. The organic phase was dried over sodium sulphate, the solvent was removed in vacuo and the residue was triturated with hexane to give 6.8 g (53% yield) of intermediate c as a brown solid.

In a third experiment, 2-[[(4-methylphenyl)sulfonyl]oxy]-acetonitrile was used as reagent b. Specifically, 2-Nitrophenol (10.0 g, 72 mmol), 2-[[(4-methylphenyl)sulfonyl]oxy]-acetonitrile (0.9 eq) and $K_2CO_3$ (2 eq) were refluxed in acetonitrile for 20 hours. The solvent was evaporated and the residue was partitioned between water and ethyl acetate. The organic layer was washed three times with an aqueous solution of $K_2CO_3$. The organic phase was dried over sodium sulphate, the solvent was removed in vacuo and the residue was triturated with hexane to give 10.3 g (80% yield) of intermediate c as a light brown solid.

In an alternative step (i), the following intermediate was prepared.

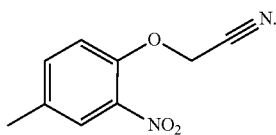

4-Methyl-2-nitrophenol was used as starting material a and chloroacetonitrile was used as reagent b. Specifically, 4-methyl-2-nitrophenol (60.0 g), chloroacetonitrile (1.4 eq), NaI (0.05 eq) and $K_2CO_3$ (1.2 eq) were heated in acetone (8 vol) at 60° C. for 20 hours. The product was recrystallized to give 82% yield of intermediate c.

In step (ii), intermediate c was reduced and cyclised to give the following fuel additive e:

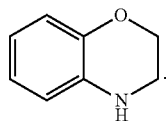

Specifically, 2-(2-nitrophenoxy)acetonitrile (2.0 g, 11 mmol), pTSA (50 mg), 10% Pd/C (100 mg) were stirred in ethanol (35 ml) under 50 bar $H_2$ at 50° C. for 2 hours. The reaction mixture was filtered, the solvent was evaporated, the residue was taken up into diethyl ether and filtered to remove solids. The solvent was removed in vacuo to give 1.34 g (88% yield) of fuel additive e as a clear brown oil.

In an alternative step (ii), the following fuel additive e was prepared:

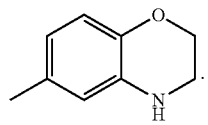

Specifically, intermediate c (2.0 g, 11 mmol), $NH_3$ in MeOH, 5% Pd/C (1 to 2 mol %) were stirred in ethanol under 10 bar $H_2$ at 50° C. for 20 hours. In spite of the lower pressure of $H_2$, approximately 68% yield of fuel additive e was nonetheless obtained.

Similar experiments were carried out in which: a platinum catalyst was used in place of the palladium catalyst; pTSA was used as a reaction additive in place of $NH_3$ in MeOH; HCl was used as a reaction additive in place of $NH_3$ in MeOH; or no reaction additive was used. Each of these reactions product fuel additive e at a good but lower yield than that obtained using $NH_3$ in MeOH.

Further experiments were conducted using $NH_3$ in MeOH as a reaction additive. The experiments showed that yields are highest where ammonia is used in an amount of from 2 to 4 molar equivalents as compared to intermediate c. The advantageous effects of using ammonia as a reaction additive were observed using both palladium and rhodium catalysts. Experiments also showed that it is preferable to carry out the reaction in the absence of water. Temperatures of lower than 70° C. also gave better yields. Experiments showed that the use of a rhodium catalyst gave a slightly improved yield, whereas the use of a vanadium and nickel catalyst reduced the yield, as compared to the palladium catalyst.

Example 2

Preparation of Fuel Additive e According to Embodiment (2)

In step (i), the following intermediate c was prepared using a variety of reagents b:

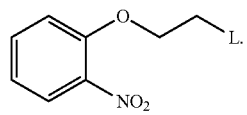

In a first experiment, chlorobromoethane was used as reagent b. Specifically, a mixture of 2-nitrophenol (5.0 g), chlorobromoethane (4 eq) and $K_2CO_3$ (2 eq) was heated at reflux in MeCN (100 ml) for 2.5 hours, the solvent was evaporated and partitioned between ethyl acetate and water. The organic phase was dried over sodium sulphate, the solvent was evaporated and the residue was triturated with hexane to give 6.8 g (94% yield) of intermediate c as a light yellow solid.

In a second experiment, dibromoethane was used as reagent b. Specifically, a mixture of 2-nitrophenol (10.0 g, 72 mmol), dibromoethane (5 eq) and $K_2CO_3$ (2 eq) was refluxed in acetonitrile (200 ml) for 2 hours. The reaction mixture was partitioned between water and diethyl ether, the organic layer was dried over sodium sulphate, evaporated and re-dissolved in a small amount of diethyl ether. The insoluble material was removed and the organic solvent was evaporated to give 15.8 g (89% yield) of intermediate c as a yellow oil.

In a third experiment, 2-bromoethanol was used as reagent b. Specifically, a mixture of 2-nitrophenol (10 g, 72 mmol), 2-bromoethanol (4 eq) and $K_2CO_3$ (2.0 eq) was refluxed in MeCN (75 ml) for 4 hours, the organic solvent was evaporated, the residue was partitioned between diethyl ether and water, the organic layer was separated, washed with water, dried over sodium sulphate and the solvent was evaporated in vacuo. The residue was purified by column chromatography (1:1 ethyl acetate/hexane) and afforded 10.2 g (77% yield) of intermediate c as a yellow oil.

In an alternative step (i), the following intermediate c was prepared:

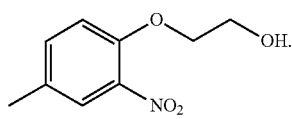

4-Methyl-2-nitrophenol was used as starting material a and ethylene carbonate was used as reagent b. Starting material a (100 g, 0.653 mol), reagent b (1 eq) and potassium carbonate (0.04 equiv) were heated at reflux (137° C.) in 4-methyl-2-pentanol (400 mL) for 37 hours. HPLC analysis of the reaction mixture confirmed 92% conversion and 89% selectivity for material c.

In step (ii), intermediate c was reduced and cyclised to give the following fuel additive e:

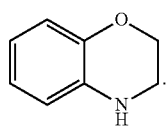

In a first experiment, intermediate c in which L is Cl (6.0 g, 30 mmol), $PtO_2$ (50 mg) and sodium acetate (1 eq) in ethyl acetate (100 ml) was hydrogenated at 10 bar and 25° C. for 2 hours. The reaction mixture was filtered and the resulting red oil was extracted in ethyl acetate, $Et_3N$ (1 eq) and NaI (200 mg) were added and the mixture was refluxed for 16 hours, to afford fuel additive e in 37% yield.

In a second experiment, intermediate c in which L is Br (3.0 g, 12.2 mmol), sodium acetate (1 eq) and $Pt_2O$ (10 mg) in ethyl acetate (30 ml) was hydrogenated at 10 bar and 25° C. for 18 hours. The mixture was filtered, and the brown oil was taken up into ethyl acetate (25 ml) and $Et_3N$ (2 ml) and refluxed 6 hours, to give a product which comprises 80% of fuel additive e (measured using $^1$H-NMR).

In an alternative step (ii), the following reaction was conducted:

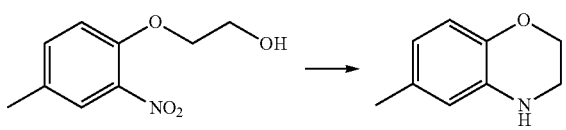

Screening work was carried out to determine whether a one-pot reaction was viable. The following conditions were shown to give fuel additive e in a promising yield:

| Catalyst | Additive | $H_2$ (bar) | Solvent | Temperature (° C.) | Yield e (%) |
|---|---|---|---|---|---|
| 5% Pd/C | HCOONa | 10 | mesitylene | 145 | 63 |
| 10% Pd/C | HCOONa | 10 | toluene | 140 | 11 |

Following the successful results obtained using Pd/C, the same transformation was conducted using different nickel (Raney-Ni and Ni—$SiO_2/Al_2O_3$) and cobalt (Raney-Co) catalysts.

A solution of intermediate c (1.97 g, 10 mmol, 0.05 M) in THF/Toluene (200 mL, 1:1) was passed through a catalyst bed at 135° C., 2 bar $H_2$ and at a rate of 1 mL/min. After approximately 6 to 8 hours of continuous circulation of the eluent stream, GC analysis indicated complete conversion of intermediate c. Complete conversion of intermediate c was observed, with the fuel additive e produced in each of the experiments. Higher yields were obtained when Raney-Ni and Raney-Co were used.

Further experiments were conducted using different nickel catalysts in a mesitylene solvent system. Two nickel catalysts were tested: Raney-Ni (slurry form in water) and Ni(65 wt %)/$SiO_2/Al_2O_3$ (20 mg, 10 mol %).

The catalyst was added to an argon flushed stainless steel autoclave (300 mL). To this was added intermediate c (394 mg, 2.0 mmol) followed by mesitylene (10 mL). The autoclave was sealed, charged to 7 bar with hydrogen and heated to 50° C. for 1 hour before raising the temperature to 170° C. The reaction was held at this temperature for 20 hours, before cooling to room temperature and sampling for UPLC (MeCN) analysis. LC analysis indicated complete conversion of intermediate c to give 83% and 87% yield of the fuel additive e for the Raney-Ni and Ni—$SiO_2/Al_2O_3$ catalysts, respectively.

Further one-pot experiments were conducted to investigate the use of different reaction materials and conditions in steps (iia") and (iib"). The same compound used as intermediate c in Example 1 was used in these experiments.

The following reaction materials and conditions were used:

| | Step (iia") | | | | Step (iib") | | | | |
|---|---|---|---|---|---|---|---|---|---|
| Solvent | Cat | $H_2$ source | Temp | Time | Solvent | Cat | $H_2$ source | Temp | Time |
| Toluene | Pd/C (5%) | $H_2$ (10 bar) $HCO_2Na$ (3eq) | 50° C. | 5 hr | Mesitylene | As before | — | 145° C. | 14 d |
| Toluene | Pd/C (10%) | $H_2$ (10 bar) $HCO_2Na$ (3eq) | 50° C. | 2 hr | As before | As before | — | 145° C. | 68 hr |
| Mesitylene[1] | Raney-Ni (0.3 eq) | $H_2$ (6 bar) | 70° C. | 54 hr | As before | As before | As before | 150° C. | 46 hr |
| Methanol | Raney-Ni (0.3 eq) | $H_2$ (6 bar) | 50° C. | 2 hr | Mesitylene | As before | — | 150° C. | 18 hr |
| Methanol | Raney-Ni (0.3 eq) | $H_2$ (6 bar) | 50° C. | 2 hr | Mesitylene | +Raney-Ni (0.3 eq) | — | 150° C. | 20 hr |
| Methanol | Raney-Ni (0.3 eq) | $H_2$ (6 bar) | rt | 3 hr | Mesitylene | As before | — | 150° C. | 22 hr |

| | Step (iia″) | | | | Step (iib″) | | | | |
|---|---|---|---|---|---|---|---|---|---|
| Solvent | Cat | H₂ source | Temp | Time | Solvent | Cat | H₂ source | Temp | Time |
| Methanol | Raney-Ni (0.3 eq) | H₂ (6 bar) | rt | 3 hr | Mesitylene | +Raney-Ni (0.3 eq) | — | 150° C. | 55 hr |
| Methanol | Raney-Ni (0.3 eq) | H₂ (6 bar) | rt | 24 hr | Mesitylene | +Raney-Ni (0.25 eq) | — | 150° C. | 86 hr |

[1] A one-step reaction, but in which different reaction conditions were used in steps (iia″) and (iib″)

Where the solvent was changed between steps (iia″) and (iib″), the original solvent was removed by distillation. Where hydrogen was removed following step (iia″), this was carried out by simply venting the reaction environment.

Fuel additive e was produced in each of the experiments. The best yields were obtained when an aprotic solvent, in particular mesitylene, was used in both steps (iia″) and (iib″). Improved yields were also obtained when extra catalyst was added in step (iib″).

Example 3

Preparation of Fuel Additive e According to Embodiment (3)

In step (i), the following intermediate c was prepared:

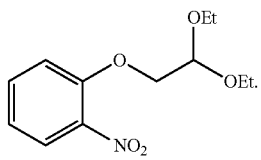 [SMILES: CCOC(COc1ccccc1[N+](=O)[O-])OCC]

Bromoacetaldehyde diethylacetal was used as reagent b. Specifically, a mixture of 2-nitrophenol (5.0 g, 36 mmol), bromoacetaldehyde diethylacetal (1 eq) and K₂CO₃ (1 eq) was heated in NMP (30 ml) to 120° C. for 16 hours, then cooled to ambient temperature, added to aq K₂CO₃ and extracted into diethylether. The organic phase was washed three times with aq K₂CO₃, dried over sodium sulphate and evaporated in vacuo to give 8.5 g (92% yield) of intermediate c as an orange oil.

In an alternative step (i), the following intermediate c was prepared:

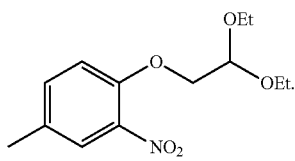

Chloroacetaldehyde dimethylacetal was used as reagent b. Specifically, a mixture of 4-methyl-2-nitrophenol (20.0 g), chloroacetaldehyde dimethylacetal (1.3 eq), NaI (0.1 eq) and K₂CO₃ (1.1 eq) was heated in NMP (4 vol) to 110-150° C. for 3 days to give 97% yield of crude intermediate c. A similar experiment was successfully conducted in which DMF was used as the solvent instead of NMP. Further similar experiments were also successfully conducted in the absence of K₂CO₃ and in the absence of both K₂CO₃ and NaI.

In step (ii), intermediate c was reduced and cyclised to give the following fuel additive e:

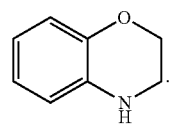

Specifically, intermediate c (2.0 g, 8 mmol), 10% Pd/C (100 mg), and pTSA (50 mg) hydrogenated at 30 bar in dioxane (30 ml) at 25° C. for 2 hours and then the temperature raised to 100° C. and maintained at this temp overnight. TLC analysis of the reaction mixture confirmed the reduction of the nitro group to an amino group, but minimal cyclisation was observed. 1 ml of concentrated HCl was added and hydrogenated at 50° C. and 40 bar for 2 hours. Sampling confirmed that no acetal was left in the reaction, which was consequently filtered and diluted with water to give a pinkish solid. TLC analysis showed an impure mixture containing fuel additive e.

In an alternative step (ii), the intermediate c from alternative step (i) was converted into the following compound:

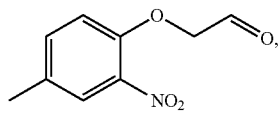

i.e. an intermediate c of embodiment (6).

Specifically, in a first experiment, intermediate c was hydrolysed in acetone/HCl at 50° C. for 43 hours. Good conversion into the intermediate c of embodiment (6) was observed. In a second experiment, intermediate c was hydrolysed in a mixture of acetonitrile (8 vol), water (12 vol) and HCl (37% solution, 0.5 eq) at 65° C. After 27 hours, 99% conversion was observed. The intermediate c of embodiment (5) may then be converted into fuel additive e by hydrogenation methods.

In a further alternative step (ii), the intermediate c from alternative step (i) was reduced to form the following intermediate product:

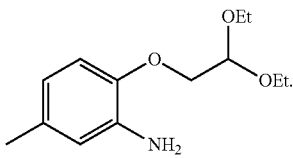 [SMILES: CCOC(COc1ccc(C)cc1N)OCC]

Specifically, intermediate c (2.0 g) in the presence of 5% Pd/C (0.5 mol %) was hydrogenated at 10 bar $H_2$ in ethanol (15 vol) at 50° C. for 8 hours. Full conversion of the nitro group to the amine was observed to give a very clean intermediate product. The intermediate product may then be converted into fuel additive e by hydrolysis followed by ring closing.

Example 4

Preparation of Fuel Additive e According to Embodiment (5)

The following intermediate d was prepared by reacting 5-methyl-2-nitrophenol with chloroacetic acid, followed by reduction of the amide to an amine and acid catalysed ring closing:

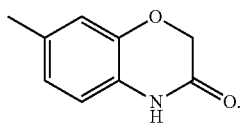

Using a number of different methods, intermediate d was converted to the following fuel additive e:

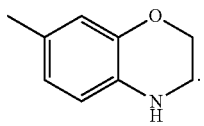

In a first experiment, sodium bis(2-methoxyethoxy)aluminium hydride 70% w/w in toluene (461 kg, 1596 mol, 2.05 eq) was added over 6.5 hours, maintaining the temperature at 20±2° C., to intermediate d (127 kg, 778 mol, KF 0.04%), toluene (1101 kg, 10 eq vol). The resulting clear red-orange solution was maintained at 20±2° C. for 24 hours then sampled for analysis. HPLC analysis of the product showed 99.75% conversion, with 81.9% fuel additive e. The reaction mixture was quenched with NaOH, and extracted with toluene. The toluene solution was washed three times with water, the solvent was evaporated and the residue was purified by vacuum distillation to yield 158 kg (85.3% yield) of fuel additive e.

In a second experiment, lithium aluminium hydride pellets (76.65 g, 1.6 eq) were stirred under nitrogen in THF (2.5 L) then cooled to <10° C. Intermediate d (206 g) was added portion wise to the lithium aluminium hydride slurry, while maintaining the temperature <10° C. The reaction mixture was stirred at room temperature for 16 hours. The mixture was quenched with water, 15% aqueous NaOH was added and the slurry was stirred for 16 hours, filtered and extracted with EtOAc. The organic solvent was evaporated to a brown oil, which was distilled (120° C., 0.05 mmHg) to yield 175 g (93%) of fuel additive e.

In a third method, intermediate d (10 g, 61 mmol) was suspended in dry THF (80 ml), the slurry was cooled to 0 to 5° C. and $BH_3$.THF (1.5 eq) was added. The reaction mixture was allowed to warm to ambient temperature, then heated to 60° C. for 16 hours, quenched with methanol and aqueous 1M HCl. The solvent was evaporated, the residue was basified with NaOH and extracted into diethyl ether. The ether phase was washed twice with water, dried over magnesium sulfate and the solvent was evaporated to give 9 g (99%) of fuel additive e as a yellow oil.

Example 5

Preparation of Intermediate c According to Embodiment (6)

In step (i), the following intermediate c was prepared:

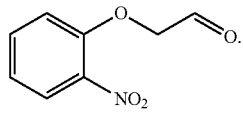

Chloroacetaldehyde was used as reagent b. Specifically, 2-nitrophenol (10.0 g, 72 mmol), aqueous chloroacetaldehyde (50%) (2 eq), $NaHCO_3$ (1.1 eq), KBr (0.12 eq) and $NMeBu_3Cl$ (0.02 eq) were stirred in toluene (50 ml) and water (20 ml) at 65° C. for 3 hours. TLC analysis showed a complex mixture in which intermediate c was present.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A method for preparing a fuel additive e having the formula:

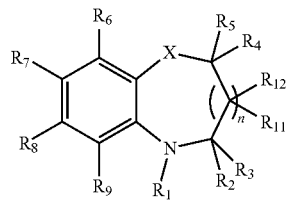

where: $R_1$ is hydrogen;

$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;

$R_6$, $R_7$, $R_8$ and $R_9$ are each independently selected from hydrogen, alkyl, alkoxy, alkoxy-alkyl, secondary amine and tertiary amine groups;

X is selected from —O— or —$NR_{10}$—, where $R_{10}$ is selected from hydrogen and alkyl groups; and n is 0 or 1, said method comprising carrying out the following reactions:

(i) addition of an alkylating agent b to starting material a:

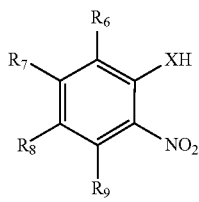

a to form an intermediate c; and (ii) ring closing intermediate c to form fuel additive e, wherein the alkylating agent b and intermediate c are selected from:

where: each L in alkylating agent b is independently selected from leaving groups or both L groups together form the group —O—C(O)—O—;

each $R_{13}$ is independently selected from hydrogen and alkyl groups, or both $R_{13}$ groups together with the —O—C—O— group to which they are attached form a 1,3-dioxolane or 1,3-dioxane group; and $R_{14}$ is selected from hydrogen and alkyl groups.

2. A method according to claim 1, wherein step (i) is carried out in the presence of a base selected from:
   inorganic bases, and
   organic bases.

3. A method according to claim 1, wherein step (i) is carried out in the presence of a catalyst, wherein the catalyst is selected from acids, zeolites, metal catalysts, halogen exchange catalysts and phase transfer catalysts.

4. A method according to claim 1, wherein step (i) is carried out in the presence of a solvent selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile, dichloromethane, dichloroethane, chloroform and water.

5. A method according to claim 1, wherein step (i) may be carried out at a temperature of greater than 40° C.

6. A method according to claim 1, wherein in alkylating agent b each L is independently selected from: halides, sulfonates, substituted aryloxy groups and hydroxy groups.

7. A method according to claim 1, wherein step (ii) is carried out in the presence of a hydrogen source and a hydrogenation catalyst.

8. A method according to claim 7, wherein the hydrogenation catalyst is selected from palladium, platinum, nickel and rhodium catalysts.

9. A method according to claim 7, wherein the hydrogen source is hydrogen gas at a pressure of from 1 to 80 bar.

10. A method according to claim 7, wherein step (ii) is carried out at a temperature of at least 20° C.

11. A method according to claim 7, wherein step (ii) is carried out in the presence of an acid.

12. A method according to claim 1, wherein the alkylating agent b and intermediate c are selected from:

| alkylating agent b | intermediate c |
|---|---|
| (2) 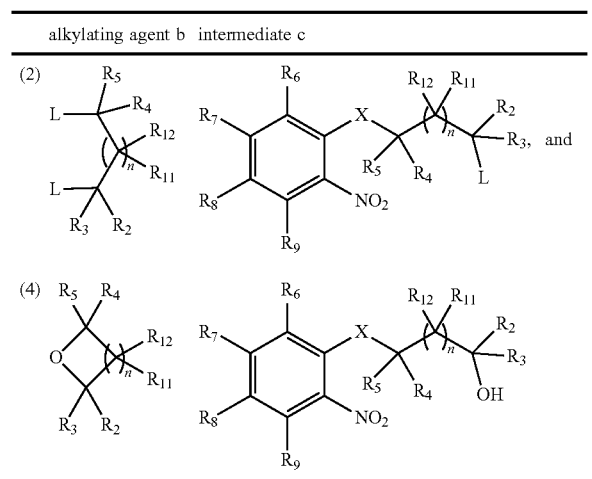 | |
| (4) | | provided that in alkylating agent b both L groups together form the group —O—C(O)—O— or at least one of the L groups is selected from —OH, and wherein step (ii) comprises sub-steps (iia) and (iib), where the one of sub-steps (iia) and (iib) are carried out in the presence of a hydrogen source and a hydrogenation catalyst, and the other of sub-steps (iia) and (iib) comprises replacing the hydroxyl group with a halogen in a halogenation reaction.

13. A method according to claim 1, wherein alkylating agent b and intermediate c are selected from:

| alkylating agent b | intermediate c |
|---|---|
| (5) 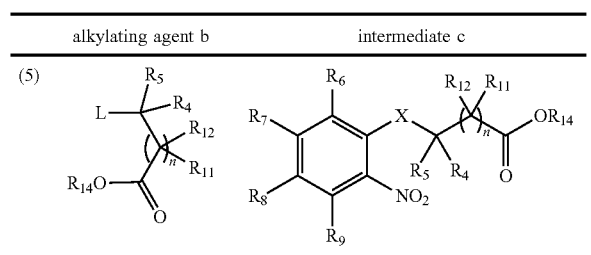 | | and wherein step (ii) comprises the following sub-steps:

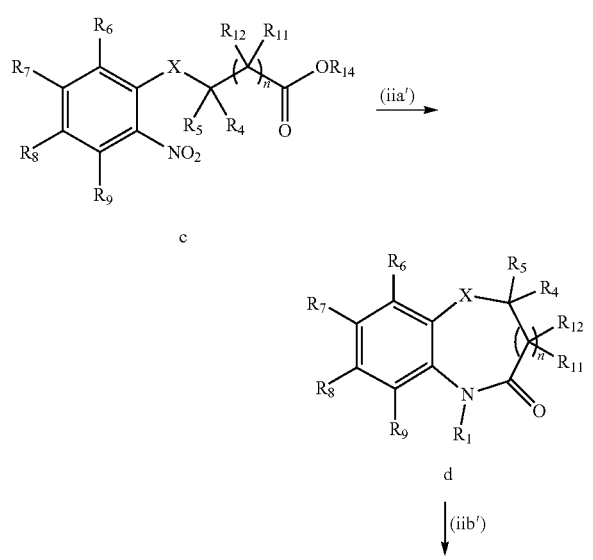

14. A method according to claim 13, wherein the sub-step (iia') is carried out in the presence of a hydrogen source and a hydrogenation catalyst.

15. A method according to claim 1, wherein the alkylating agent b and intermediate c are selected from:

| alkylating agent b | intermediate c |
|---|---|
| (1) 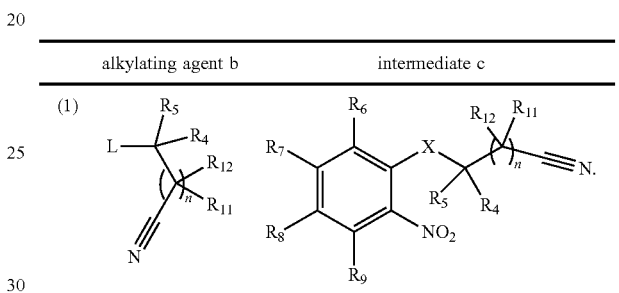 | |

16. A method according to claim 1, wherein the method is a batch process in which the fuel additive is produced in a batch quantity of greater than 100 kg.

17. A method according to claim 1, wherein the method is a continuous process.

18. A process for preparing a fuel for a spark-ignition internal combustion engine, said process comprising:

preparing a fuel additive e having the formula:

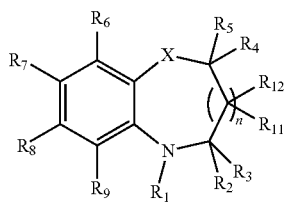

where: $R_1$ is hydrogen;

$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;

$R_6$, $R_7$, $R_8$ and $R_9$ are each independently selected from hydrogen, alkyl, alkoxy, alkoxy-alkyl, secondary amine and tertiary amine groups;

X is selected from —O— or —$NR_{10}$—, where $R_{10}$ is selected from hydrogen and alkyl groups; and n is 0 or 1, comprising carrying out the following reactions:
(i) addition of an alkylating agent b to starting material a:

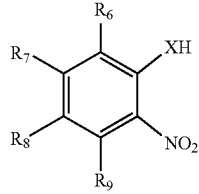

to form an intermediate c; and
(ii) ring closing intermediate c to form fuel additive e, wherein the alkylating agent b and intermediate c are selected from:

| alkylating agent b | intermediate c |
|---|---|
| (1) | |
| (2) | |
| (3) | |
| (4) | |
| (5) | |
| (6) | | where: each L in alkylating agent b is independently selected from leaving groups or both L groups together form the group —O—C(O)—O—;

each $R_{13}$ is independently selected from hydrogen and alkyl groups, or both $R_{13}$ groups together with the —O—C—O— group to which they are attached form a 1,3-dioxolane or 1,3-dioxane group; and $R_{14}$ is selected from hydrogen and alkyl groups; and blending the fuel additive e with a base fuel.

* * * * *